US006713450B2

(12) United States Patent
Frangione et al.

(10) Patent No.: US 6,713,450 B2
(45) Date of Patent: Mar. 30, 2004

(54) SYNTHETIC IMMUNOGENIC BUT NON-AMYLOIDOGENIC PEPTIDES HOMOLOGOUS TO AMYLOID β FOR INDUCTION OF AN IMMUNE RESPONSE TO AMYLOID β AND AMYLOID DEPOSITS

(75) Inventors: Blas Frangione, New York, NY (US); Thomas Wisniewski, Staten Island, NY (US); Einar M. Sigurdsson, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/861,847

(22) Filed: May 22, 2001

(65) Prior Publication Data

US 2002/0077288 A1 Jun. 20, 2002

Related U.S. Application Data

(60) Provisional application No. 60/205,578, filed on May 22, 2000.

(51) Int. Cl.$^7$ .......................... A61K 38/00; A61K 39/00; C07K 7/00
(52) U.S. Cl. ........................ 514/12; 530/300; 424/198.1
(58) Field of Search ...................... 514/14, 12; 530/300; 424/184.1, 185.1, 193.1, 198.1

(56) References Cited

FOREIGN PATENT DOCUMENTS

| WO | WO 95/31996 | 11/1995 | .......... A61K/38/17 |
|----|-------------|---------|----------------------|
| WO | WO 96/39834 | 12/1996 | .......... A01N/43/40 |
| WO | WO 99/279244 | 6/1999 | .......... A61K/38/00 |
| WO | WO 99/279949 | 6/2000 | .......... A61K/38/17 |
| WO | WO 00/72880 | 12/2000 | ......... A61K/39/395 |

OTHER PUBLICATIONS

Kitada et al., WO9417197, Aug. 4, 1994.*
Zhou et al., Nucleic Acids Res., 18:5554, 1990.*
Yamada et al., Biochem. Biophys. Res. Commun., 149:665–671, 1987.*
Frenkel, D. et al.: "Modulation of Alzheimer's beta–amyloid neurotoxicity by site–directed single–chain antibody." Neuroimmunomodulation, vol. 6, No. 6, Nov. 1999, p. 444 XP00800088, 4$^{th}$ International Congress of the International Society for Neuroimmunomodulation; Lugano, Switzerland; Sep. 29–Oct. 2, 1999. ISSN: 1021–7401, abstract.
Solomon, B. et al.: "Disaggregation of Alzheimer Beta–Amyloid by Site–Directed Mab" Proceedings Of The National Academy Of Sciences of USA, National Academy Of Science, Washington, US, vol. 94, Apr. 1997, pp. 4109–4112, XP002911322, ISSN: 0027–8424, the whole document.
Sigurdsson, Einar M. et al.: "Immunization with a nontoxic/nonfibrillar amyloid–beta homologus peptide reduces Alzheimer's disease–associated pathologhy in transgenic mice." American Journal Of Pathology, vol. 159, No. 2, Aug. 2001, pp. 439–447, XP008000840, ISSN: 0002–9440, the whole document.

Schenk, Dale et al.: "Immunization with amyloid–β attenuates Alzheimer–disease–like pathology in the PDAPP mouse." Nature, 1999;400: pp. 173–177.
Aguado, T. et al.: "Meeting Report—Novel adjuvants currently in clinical testing Nov. 2–4, 1998, Foundation Mérieux, Annecy, France: A meeting sponsored by the World Health Organization." Vaccine 17 (1999); pp. 2321–2328.
Pallitto, Monica M. et al.: "Recognition Sequence Design for Peptidyl Modulators of β–Amyloid Aggregation and Toxicity." Biochemistry 1999, 38, pp. 3570–3578.
Futaki, S. et al.: "Arginine–rich peptides: An abundant source of membrane–permeable peptides having potential as carriers for intracellular protein delivery." J Biol. Chem. 2001, Feb. 23; 276 (8): 5836–40, abstract.
Martinez–Fong, D. et al.: "Nonenzymatic glycosylation of poly–L–lysine: a new tool for targeted gene delivery." Hepatology 1994 Dec.; 20(6): 1602–8.
Schwarzenberger, P. et al.: "Poly–L–lysine–based molecular conjugate vectors: a high efficiency gene transfer system for human progenitor and leukemia cells." Am J Med Sci 2001 Feb.; 321 (2): 129–36.
Wang, Y. et al., "Endocytosis of horseradish peroxidase–poly–lysine conjugate by glomerular epithelial cells: an in vitro study." J Pathol 1989 Oct.; 159(2): 159–67.
Shen, W.C. et al.: "Disulfide spacer between methotrexate and poly(D–lysine). A probe for exploring the reductive process in endocytosis." J Biol Chem 1985 Sep 15; 260(20): 10905–8.
Peterson, P.K. et al.: "Polyamino acid enhancement of bacterial phagocytosis by human polymorphonuclear leukocytes and peritoneal macrophages." Infect Immun 1984 Feb.; 43(2): 561–6.
Deierkauf F.A., et al.: "Phygocytosis by rabbit polymorphonuclear leukocytes: the effect of albumin and polyamino acids on latex uptake." J Cell Physiol 1977 Aug.; 92(2): 169–75.
Di Nicola, M. et al.: "Large–scale feasibility of gene transduction into human CD34+ cell derived dendritic cells by adenoviral/polycation complex." Br J Haematol 2000 Oct.; 111(1):344–50.
Buschle M. et al.: "Transloading of tumor antigen–derived peptides into antigen–presenting cells." Proc Natl Acad Sci USA 1997 Apr. 1;94 (7): 3256–61.
Farmer, J.L. et al.: "Human immune response to cationized proteins. II. Characterization of interaction of cationized diphtheria toxoid with human mononuclear cells." Cell Immunol 1993 Jan.; 146(1): 198–209.

* cited by examiner

Primary Examiner—Gary Kunz
Assistant Examiner—Sharon L. Turner
(74) Attorney, Agent, or Firm—Darby & Darby

(57) ABSTRACT

The present invention relates to synthetic immunogenic but non-amyloidogenic peptides homologous to amyloid β which can be used alone or conjugated to an immunostimulatory molecule in an immunizing composition for inducing an immune response to amyloid β peptides and amyloid deposits.

30 Claims, 10 Drawing Sheets

SYNTHETIC IMMUNOGENIC BUT NON-AMYLOIDOGENIC PEPTIDES HOMOLOGOUS TO AMYLOID β FOR INDUCTION OF AN IMMUNE RESPONSE TO AMYLOID β AND AMYLOID DEPOSITS

CROSS-REFERENCE TO RELATED APPLICATIONS

The present application claims the benefit of priority from U.S. provisional application No. 60/205,578, filed May 22, 2000, the entire content of which is hereby incorporated by reference.

GOVERNMENT LICENSE RIGHTS

The experiments performed in this application were supported in part by the National Institutes of Health, Grant Nos. AG15408, AR02594, AG17617, and AG05891. The U.S. Government has a paid-up license in this invention and the right in limited circumstances to require the patent owner to license others on reasonable terms as provided for by the terms of Grant NOs: AG15408, AR02594, AG17617, and AG05891.

BACKGROUND OF THE INVENTION

1. Field of the Invention

The present invention relates to the field of amyloid β peptides and a method for inducing an immune response to amyloid β peptides and amyloid deposits.

2. Description of the Background Art

Alzheimer's disease (AD) is the most common form of late-life dementia in adults (Soto et al., 1994), constituting the fourth leading cause of death in the United States. Approximately 10% of the population over 65 years old is affected by this progressive degenerative disorder that is characterized by memory loss, confusion and a variety of cognitive disabilities. Neuropathologically, AD is characterized by four major lesions: a) intraneuronal, cytoplasmic deposits of neurofibrillary tangles (NFT), b) parenchymal amyloid deposits called neuritic plaques, c) cerebrovascular amyloidosis, and d) synaptic and neuronal loss. One of the key events in AD is the deposition of amyloid as insoluble fibrous masses (amyloidogenesis) resulting in extracellular neuritic plaques and deposits around the walls of cerebral blood vessels. The major constituent of the neuritic plaques and congophilic angiopathy is amyloid β (Aβ), although these deposits also contain other proteins such as glycosaminoglycans and apolipoproteins.

Aβ is a 4.1–4.3 kDa hydrophobic peptide that is codified in chromosome 21 as part of a much longer amyloid precursor protein APP (Muller-Hill et al., 1989). The APP starts with a leader sequence (signal peptide), followed by a cysteine-rich region, an acidic-rich domain, a protease inhibitor motif, a putative N-glycosylated region, a transmembrane domain, and finally a small cytoplasmic region. The Aβ sequence begins close to the membrane on the extracellular side and ends within the membrane. Two-thirds of Aβ faces the extracellular space, and the other third is embedded in the membrane (Kang et al., 1987 and Dyrks et al., 1988). Several lines of evidence suggest that amyloid may play a central role in the early pathogenesis of AD.

Evidence that amyloid may play an important role in the early pathogenesis of AD comes primarily from studies of individuals affected by the familial form of AD (FAD) or by Down's syndrome. Down's syndrome patients have three copies of the APP gene and develop AD neuropathology at an early age (Wisniewski et al., 1985). Genetic analysis of families with hereditary AD revealed mutations in chromosome 21, near or within the Aβ sequence (Forsell et al., 1995), in addition to mutations within the presenilin 1 and 2 genes. Moreover, it was reported that transgenic mice expressing high levels of human mutant APP progressively develop amyloidosis in brain (Games et al., 1995). These findings appear to implicate amyloidogenesis in the pathophysiology of AD. In addition, Aβ fibrils are toxic in neuronal culture (Yankner et al., 1989) and to some extent when injected into animal brains (Sigurdsson et al., 1996 and 1997).

Furthermore, several other pieces of evidence suggest that the deposition of Aβ is a central triggering event in the pathogenesis of AD, which leads subsequently to NFT formation and neuronal loss. The amyloid deposits in AD share a number of properties with all the other cerebral amyloidoses, such as the prion related amyloidoses, as well as the systemic amyloidoses. These characteristics are: 1) being relatively insoluble; 2) having a high β-sheet secondary structure, which is associated with a tendency to aggregate or polymerize; 3) ultrastructurally, the deposits are mainly fibrillary; 4) presence of certain amyloid-associated proteins such as amyloid P component, proteoglycans and apolipoproteins; 5) deposits show a characteristic apple-green birefringence when viewed under polarized light after Congo red staining.

The same peptide that forms amyloid deposits in AD brain was also found in a soluble form (sAβ) normally circulating in the human body fluids (Seubert et al., 1992 and Shoji et al., 1992). Zlokovic et al. (1994), reported that the blood-brain barrier (BBB) has the capability to control cerebrovascular sequestration and transport of circulating sAβ, and that the transport of the sAβ across the BBB was significantly increased when sAβ was perfused in guinea pigs as a complex with apolipoprotein J (apoJ). The sAβ-apoJ complex was found in normal cerebrospinal fluid (CSF; Ghiso et al., 1994) and in vivo studies indicated that sAβ is transported with apoJ as a component of the high density lipoproteins (HDL) in normal human plasma (Koudinov et al., 1994). It was also reported by Zlokovic et al. (1996), that the transport of sAβ across the BBB was almost abolished when the apoJ receptor gp330 was blocked. It is believed that the conversion of sAβ to insoluble fibrils is initiated by a conformational modification of the 2–3 amino acid longer soluble form. It has been suggested that the amyloid formation is a nucleation-dependent phenomena in which the initial insoluble "seed" allows the selective deposition of amyloid (Jarrett et al., 1993).

Peptides containing the sequence 1–40 or 1–42 of Aβ and shorter derivatives can form amyloid-like fibrils in the absence of other protein (Soto et al., 1994), suggesting that the potential to form amyloid resides mainly in the structure of Aβ. The relation between the primary structure of Aβ and its ability to form amyloid-like fibrils was analyzed by altering the sequence of the peptide. Substitution of hydrophilic residues for hydrophobic ones in the internal Aβ hydrophobic regions (amino acids 17–21) impaired fibril formation (Hilbich et al., 1992), suggesting that Aβ assembly is partially driven by hydrophobic interactions. Indeed, larger Aβ peptides (Aβ1-42/43) comprising two or three additional hydrophobic C-terminal residues are more amyloidogenic (Jarrett et al., 1993). Secondly, the conformation adopted by Aβ peptides is crucial in amyloid formation. Aβ peptides incubated at different pH, concentrations and solvents can have either a mainly α-helical, random coil, or a β-sheet secondary structure (Barrow et al., 1992; Burdick et al., 1992 and Zagorski et al., 1992). The Aβ peptide with α-helical or random coil structure aggregates slowly; Aβ with β-sheet conformation aggregates rapidly (Zagorski et al., 1992; Soto et al., 1995 and Soto et al., 1996). The importance of hydrophobicity and β-sheet secondary structure on amyloid formation also is suggested by comparison of the sequence of other amyloidogenic proteins.

Analysis of Aβ aggregation by turbidity measurements indicates that the length of the C-terminal domain of Aβ influences the rate of Aβ assembly by accelerating nucleus formation (Jarrett et al., 1993). Thus, the C-terminal domain of Aβ may regulate fibrillogenesis. However, in vitro modulators of Aβ amyloid formation, such as metal cations (Zn, Al) (Bush et al., 1994 and Exley et al., 1993) heparin sulfate proteoglycans, and apoliprotein E (Strittmatter et al., 1993) interact with the 12–28 region of Aβ. Moreover, mutations in the APP gene within the N-terminal Aβ domain yield analogs more fibrillogenic (Soto et al., 1995 and Wisniewski et al., 1991). Finally, while the C-terminal domain of Aβ invariably adopts a β-strand structure in aqueous solutions, environmental parameters determine the existence of alternative conformation in the Aβ N-terminal domain (Barrow et al., 1992; Soto et al., 1995 and Burdick et al., 1992). Therefore, the N-terminus may be a potential target site for inhibition of the initial random coil to β-sheet conformational change.

The emerging picture from studies with synthetic peptides is that Aβ amyloid formation is dependent on hydrophobic interactions of Aβ peptides adopting an antiparallel β-sheet conformation and that both the N- and C-terminal domains are important for amyloid formation. The basic unit of fibril formation appears to be the conformer adopting an antiparallel β-sheet composed of strands involving the regions 10–24 and 29–40/42 of the peptide (Soto et al., 1994). Amyloid formation proceeds by intermolecular interactions between the β-strands of several monomers to form an oligomeric β-sheet structure precursor of the fibrillar β-cross conformation. Wood et al., (1995) reported the insertion of aggregation-blocking prolines into amyloid proteins and peptides to prevent aggregation of such proteins and peptides. In this manner, the authors suggest that novel proteins can be designed to avoid the problem of aggregation as a barrier to their production without affecting the structure or function of the native protein. Thus, Wood et al. seek to produce novel proteins that would not aggregate during recombinant protein production and purification by inserting aggregation/blocking prolines into these novel peptides.

To date there is no cure or effective therapy for reducing a patient's amyloid burden or preventing amyloid deposition in AD, and even the unequivocal diagnosis of AD can only be made after postmortem examination of brain tissues for the hallmark neurofibrillary tangles (NFT) and neuritic plaques. However, there are an increasing number of publications outlining strategies for the treatment of Alzheimer's disease. Amyloid-related therapeutic strategies include the use of compounds that affect processing of the amyloid-β precursor protein (APP; Dovey et al., 2001), that interfere with fibril formation or that promote fibril disassembly (Soto et al., 1998; Sigurdsson et al., 2000; and Findeis, 2000).

Heparin sulfate (glycosoaminoglycan) or the heparin sulfate proteoglycan, perlecan, has been identified as a component of all amyloids and has also been implicated in the earliest stages of inflammation-associated amyloid induction. Kisilevsky et al. (1995) describes the use of low molecular weight (135–1,000 Da) anionic sulfonate or sulfate compounds that interfere with the interaction of heparin sulfate with the inflammation-associated amyloid precursor and the β-peptide of AD. Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin-accelerated Alzheimer's Aβ fibril formation and were able to disassemble preformed fibrils in vitro as monitored by electron micrography. Moreover, when administered orally at relatively high concentrations (20 or 50 mM), these compounds substantially arrested murine splenic inflammation-associated amyloid progression in vivo in acute and chronic models. However, the most potent compound, poly-(vinylsulfonate), was acutely toxic.

Anthracycline 4'-iodo-4'-deoxy-doxorubicin (IDOX) has been observed clinically to induce amyloid resorption in patients with immunoglobin light chain amyloidosis (AL). Merlini et al. (1995), elucidated its mechanism of action. IDOX was found to bind strongly via hydrophobic interactions to two distinct binding sites (Scatchard analysis) in five different tested amyloid fibrils, inhibiting fibrillogenesis and the subsequent formation of amyloid deposits in vitro. Preincubation of IDOX with amyloid enhancing factor (AEF) also reduced the formation of amyloid deposits. Specific targeting of IDOX to amyloid deposits in vivo was confirmed in an acute murine model. This binding is distinct from heparin sulfate binding as removal of the glycosaminoglycans from extracted amyloid fibrils with heparinases did not modify IDOX binding. The common structural feature of all amyloids is a β-pleated sheet conformation. However, IDOX does not bind native amyloid precursor light chains which suggests that the β-pleated sheet backbone alone is not sufficient to form the optimal structure for IDOX binding, and that it is the fibril cross-β-sheet quaternary structure that is required for maximal IDOX binding. It has been found that the amount of IDOX extracted from spleens is correlated with amyloid load and not circulating serum precursor amyloid levels. IDOX, however, is also extremely toxic.

The regulation and processing of amyloid precursor protein (APP) via inhibition or modulation of phosphorylation of APP control proteins has also been investigated in U.S. Pat. No. 5,385,915 and WO 9427603. Modulating proteolytic processing of APP to nucleating forms of AD has also been examined in AU 9338358 and EP569777. WO 95046477 discloses synthetic peptides of composition X-X-N-X (SEQ ID NO:69) coupled to a carrier, where X is a cationic amino acid and N is a neutral amino acid, which inhibit Aβ binding to glycosoaminoglycan. Peptides containing Alzheimer's Aβ sequences that inhibit the coupling of α-1-antichymotrypsin and Aβ are disclosed in WO 9203474.

From experiments conducted at the laboratory of the present inventors, WO 96/39834 discloses that peptides capable of interacting with a hydrophobic portion on a protein or peptide, such as Aβ, involved in amyloid-like deposit formation can be used to inhibit and structurally block the abnormal folding of such proteins and peptides into amyloid or amyloid-like deposits. The peptides which block abnormal folding of Aβ into amyloid deposits have a hydrophobic portion containing β-sheet breaking amino acid residue(s), such as proline, that reduces the propensity of the peptide for adopting a β-sheet conformation. The laboratory of the present inventors, in later reports, have demonstrated that LeuProPhePheAsp (SEQ ID NO:14), a non-amyloidogenic peptide with sequence homology to Aβ blocks fibril formation (Soto et al., 1998), and induces in vivo disassembly of fibrillar Aβ deposits (Sigurdsson et al., 2000).

Recently, the coupling of lysine residues to peptides was proposed by Pallitto et al. (1999), in the design of anti-β sheet peptides or Aβ fibrillogenesis inhibitors that have an Aβ-binding recognition sequence and a hexameric lysine aggregation disrupting element.

In vitro studies have shown that monoclonal antibodies raised against the N-terminal region of Aβ can disaggregate Aβ fibrils, maintain Aβ solubility, and prevent Aβ toxicity in cell culture (Solomon et al., 1996 and 1997).

WO 96/25435 discloses the potential for using a monoclonal antibody, which is end-specific for the free C-terminus of the Aβ1-42 peptide, but not for the Aβ1-43 peptide, in preventing the aggregation of Aβ1-42. The administration of such an Aβ end-specific monoclonal antibody is further disclosed to interact with the free C-terminal residue of Aβ1-42, thereby interfering with and disrupting aggregation that may be pathogenic in AD.

WO 98/44955 takes a different approach to avoiding the problems associated with repeated administration of pharmacological agent and discloses a method for preventing the onset of Alzheimer's Disease or for inhibiting progression of Alzheimer's Disease through the stable ectopic expression in the brain of recombinant antibodies end-specific for amyloid-β peptides.

Recently, Schenk et al. (1999) demonstrated that immunization with amyloid-β attenuated Alzheimer's disease-like pathology in PDAPP transgenic mice serving as an animal model for amyloid-β deposition and Alzheimer's disease-like neuropathologies. They reported that immunization of young animals prior to the onset of Alzheimer's disease-type neuropathologies essentially prevented the development of β-amyloid plaque formation, neuritic dystrophy and astrogliosis, whereas treatment in older animals after the onset of Alzheimer's disease-type neuropathologies was observed to reduce the extent and progression of these neuropathologies. This effect is thought to be mediated by antibodies, since peripherally administered antibodies against Aβ have been shown to reduce brain parenchymal amyloid burden (Bard et al., 2000). In addition, intranasal immunization with freshly solubilized Aβ1-40 reduces cerebral amyloid burden (Weiner et al., 2000). Two recent studies demonstrated that a vaccination-induced reduction in brain amyloid deposits resulted in cognitive improvements (Morgan et al., 2000; Janus et al., 2000).

Although the results reported by Schenk et al. provides promise for using immunomodulation as a general approach to treat Alzheimer's disease, immunization with intact amyloid-β according to Schenk et al. presents problems that make it inappropriate for human use. First, Schenk et al's experiments used transgenic mice which express a mutated human protein that is foreign to them and that has no physiological function in mice (the mouse and human Aβ peptide sequences are significantly different). However, in humans, the precursor protein (βAPP) is an endogenous protein that has a normal function. Hence, using this approach in humans with a human Aβ peptide may well lead to development of an autoimmune disorder or disease that could make matters worse not better. Second, B. Zlokovic (1997) and the present inventors have results which demonstrate that Aβ peptides, Aβ1-42 and Aβ1-40, can cross the blood brain barrier in experimental animals. Therefore, in humans, it is expected that Aβ1-42, which is used for immunization in Schenk et al., can cross the blood brain barrier and co-deposit on any existing amyloid plaques leading to increased toxicity, and may actually promote plaque formation. This has not been a problem in the PDAPP transgenic mouse model for AD because human Aβ1-42 is less toxic for the mouse; even with massive deposition of human Aβ1-42, none of the transgenic mice show significant neuronal loss. Thirdly, Schenk et al. use a toxic adjuvant to induce an immune response.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a synthetic immunogenic but non-amyloidogenic peptide homologous to amyloid β which can be used for induction of an immune response to amyloid β peptides and amyloid deposits and would overcome or avoid the complications and problems encountered in the prior art.

The synthetic immunogenic but non-amyloidogenic peptide homologous to amyloid β includes the first thirty amino acid residues of Aβ1-42 (SEQ ID NO:1), where zero, one or two of residues 17–21 are substituted with Lys, Asp, or Glu, and preferably includes an N-terminal and/or C-terminal segment of 4–10 Lys or Asp residues.

The present invention also provides a conjugate in which the peptide is cross-linked to an immunostimulatory polymer molecule.

Another aspect of the present invention is directed to an immunizing composition/vaccine which contains an immunizing effective amount of the synthetic non-amyloidogenic but immunogenic peptide homologous to amyloid β, or a conjugate thereof.

A further aspect of the present invention is directed to a method for immunotherapy to induce an immune response to amyloid β peptides and amyloid deposits.

A still further aspect of the invention is directed to molecules which include the antigen-binding portion of an antibody raised against the synthetic non-amyloidogenic but immunogenic peptide according to the present invention. Also provided are pharmaceutical compositions containing this peptide-binding molecule and a method for reducing the formation of amyloid fibrils and deposits.

BRIEF DESCRIPTION OF THE DRAWINGS

FIGS. 3C and 3D are adjacent sections (X100) double stained for interleukin-1 that recognizes microglia, and Aβ. Note the reduction of amyloid burden in the immunized mouse (FIG. 3B), and the lack of ramified microglia (FIG. 3D) surrounding Aβ plaque in the same mouse, compared to a control mouse (FIGS. 3A, 3C). The bars in FIGS. 3A and 3C are 100 μm. Abbreviations: hip=hippocampus; cx=cortex; cc=corpus callosum.

DETAILED DESCRIPTION OF THE INVENTION

Figure 1:
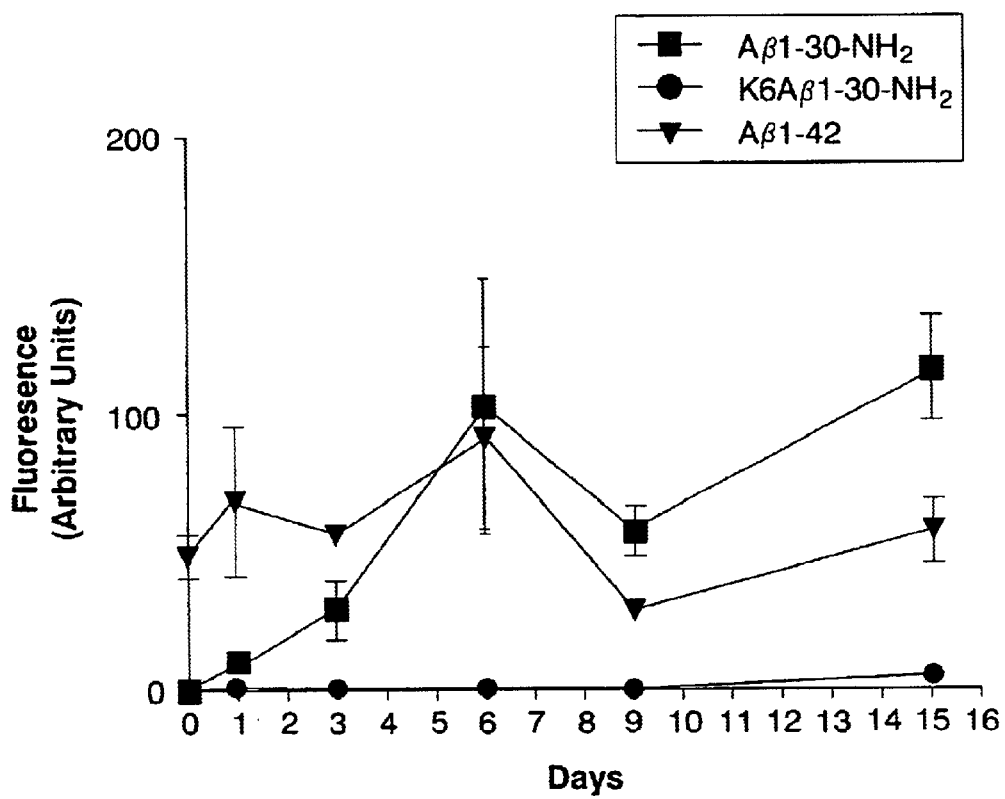
FIG. 1 shows the results of a thioflavin T fluorometric assay. Fibril formation of Aβ1-42, Aβ1-30-NH$_2$, and K6Aβ1-30-NH$_2$ (SEQ ID NO:6) was measured in vitro following incubation at 37° C. K6Aβ1-30-NH$_2$ was the only peptide that did not form fibrils at any of the time points.

The present inventors have designed synthetic non-amyloidogenic peptides homologous to amyloid β (Aβ) which have not only a reduced ability to adopt a β-sheet conformation as an antigenic source but also would have a much lower risk of leading to any toxic effects in humans. By using these synthetic non-amyloidogenic peptides, or conjugates thereof, in an immunizing composition, the present invention provides a means for rendering Aβ peptides and amyloid deposits as targets for the immune system. An important object of the present invention is therefore to provide a method for immunization which minimizes the toxicity associated with injected Aβ peptides while maximizing the immune response to Aβ peptides and amyloid deposits.

The synthetic non-amyloidogenic but immunogenic peptides homologous to Aβ according to the present invention are designed to have reduced fibrillogenic potential while maintaining the two major immunogenic sites of Aβ peptides, which are residues 1–11 and 22–28 of Aβ1-42 based on the antigenic index of Jameson et al. (1988) and results/observations obtained in the laboratory of the present inventors. Accordingly, the present inventors have based the design of the synthetic non-amyloidogenic peptide on the first thirty amino acid residues (SEQ ID NO:1) of Aβ1-42, where one or two of the hydrophobic residues at positions 17-21 of SEQ ID NO:1 are substituted with charged residues Lys, Asp, or Glu. The first thirty residues of Aβ lack the hydrophobic C-terminus of Aβ1-42 but retains the two immunogenic sites corresponding to residues 1–11 and 22–28 of SEQ ID NO:1.

By modifying one or two residues at positions 17–21 of Aβ1-30 (SEQ ID NO:1) with Lys, Asp, or Glu, which are hydrophilic residues that have a low probability of adopting β-sheet conformation, the fibrillogenic potential of the peptide is greatly reduced. SEQ ID NOs: 12 and 13 are examples of such modified Aβ1-30. Furthermore, the presence of a series of Lys or Asp residues at the N-terminus and/or C-terminus of the synthetic peptide of the present invention would further enhance immunogenicity (Werdelin, 1981) and reduce the propensity of the synthetic peptide to adopt a β-sheet conformation and form amyloid fibrils/deposits. The coupling of lysine residues to Aβ peptides of 4 to 8 residues in length has recently been proposed by Pallitto et al. (1999) in the design of anti-β-sheet peptides or Aβ fibrillogenesis inhibitors, but the use of Pallitto's peptides as immunogens has never been proposed. Polycationic amino acids have been previously used to enhance protein transport into cells by endocytosis/phagocytosis processes (Martinez-Fong et al., 1994; Wang et al., 1989; Shen et al., 1985; Peterson et al., 1984; Deierkauf et al., 1977; DiNicola et al., 2000). Buschle et al., (1997) reported that polycationic amino acids enhanced uptake of peptides by antigen presently cells, thereby initiating an immune response. They also reported that, whereas peptide uptake mediated by polylysine appears to be due to an at least transient permeabilization of cell membranes, peptide delivery in the presence of polyarginine may rely on endocytic processes.

The synthetic immunogenic but non-amyloidogenic peptide homologous to Aβ according to the present invention, which is not considered to be a peptide inhibitor of Aβ fibrillogenesis, is represented by the formula

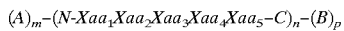

wherein:
m is 0, 4, 5, 6, 7, 8, 9, or 10;
p is 0, 4, 5, 6, 7, 8, 9, or 10;
A is Lys or Asp;
B is Lys or Asp;
n is 1 or 2;
N is residues 1–16 of SEQ ID NO:1;
C is residues 22–30 of SEQ ID NO:1;
Xaa$_1$ Xaa$_2$, Xaa$_3$, Xaa$_4$, and Xaa$_5$ are Leu, Val, Phe, Phe, and Ala, respectively, in which zero, one or two of residues Xaa$_1$, Xaa$_2$ Xaa$_3$, Xaa$_4$, and Xaa$_5$ is substituted with Lys, Asp, or Glu; and
when zero residues are substituted, then either or both of m or p is not zero.

The amino acid sequences of the peptide represented by the above formula are presented and identified as SEQ ID NOs:2–5.

The basic thirty amino acid sequence (Aβ1-30) in which zero, one or two of residues 17–21 are substituted is represented in the above formula by N-Xaa$_1$Xaa$_2$Xaa$_3$Xaa$_4$Xaa$_5$-C (SEQ ID NO:15). This thirty amino acid residue segment can be repeated (n is 2) in the synthetic peptide according to the present invention. Preferably, a polylysine or polyaspartate segment of 4 to 10 residues is present at the N-terminus and/or the C-terminus of the peptide. When no residues are substituted in residues 17–21 of Aβ1-30, the peptide has a polylysine or polyaspartate segment of 4 to 10 residues at the N-terminus and/or C-terminus. If a polylysine or polyaspartate segment is not present at the C-terminus, then the C-terminus is preferably amidated, as exemplified by SEQ ID NO:6 as a preferred embodiment. SEQ ID NO:11 is an embodiment of an unsubstituted Aβ1-30 peptide with a polylysine or polyaspartate segment of 4 to 10 residues at the C-terminus.

Furthermore, when m is 0, the N-terminal polylysine or polyaspartate segment of 4 to 10 residues is absent, and it is then preferred that either the C-terminus of the peptide be amidated to reduce the possibility that the C-terminal charge of the peptide would reduce the immunogenicity of the residue 22–28 region of Aβ or that a polylysine or polyaspartate segment of 4 to 10 residue be present at the C-terminus. Another preferred embodiment of the peptide according to the present invention is as follows:

when m is not zero, p is zero;
when p is not zero, m is zero; and
Xaa$_1$, Xaa$_2$, Xaa$_3$, Xaa$_4$, and Xaa$_5$ are Leu, Val, Phe, Phe, and Ala, respectively, in which one or two residues Xaa$_1$, Xaa$_2$, Xaa$_3$, Xaa$_4$, and Xaa$_5$ is substituted with Lys, Asp, or Glu (SEQ ID NOs:2–5).

Those of skill in the art will also appreciate that peptidomimetics of the synthetic peptide of the present invention, where the peptide bonds are replaced with non-peptide bonds, can also be used.

As is well-known in the art, the reduced fibrillogenic potential for the synthetic peptides according to the present invention can be readily determined by measuring the β-sheet conformation of the peptides using conventional techniques such as circular dichroism spectra, FT-IR, and electron microscopy of peptide suspensions.

It is also well-known that immunogens must be presented in conjunction with major histocompatibility (MHC) class II antigens to evoke an efficient antibody response. The MHC class II antigens produced by antigen-presenting cells (APCs) bind to T cell epitopes present in the immunogen in a sequence specific manner. This MHC class II-immunogen complex is recognized by CD4$^+$ lymphocytes (T$_h$ cells), which cause the proliferation of specific B cells capable of recognizing a B cell epitope from the presented immunogen and the production of B cell epitope-specific antibodies by such B cells. An additional approach to further increase immunogenicity of the synthetic peptides of the present invention is to form a conjugate with an immunostimulatory polymer molecule such as mannan (polymer of mannose), glucan (polymer of β1-2 glucose), tripalmitoyl-S-glycerine cysteine, and peptides which are currently approved for use in vaccines in humans. Such peptides approved for use in vaccines provide strong T helper cell (T$_h$) epitopes from potent immunogens such as tetanus toxin, pertussis toxin, the measles virus F protein, and the hepatitis B virus surface antigen (HBsAg). The T$_h$ epitopes selected to be conjugated to the synthetic peptide are preferably capable of eliciting T helper cell responses in large numbers of individuals expressing diverse MHC haplotypes. These epitopes function in many different individuals of a heterogeneous population and are considered to be promiscuous T$_h$ epitopes. Promiscuous T$_h$ epitopes provide an advantage of eliciting potent antibody responses in most members of genetically diverse population groups.

Moreover, the T helper cell epitopes conjugated/cross-linked to the synthetic peptide of the present invention are also advantageously selected not only for a capacity to cause immune responses in most members of a given population, but also for a capacity to cause memory/recall responses. When the mammal is human, the vast majority of human subjects/patients receiving immunotherapy with the synthetic peptide of the present invention will most likely already have been immunized with the pediatric vaccines (i.e., measles+mumps+rubella and diphtheria+pertussis+tetanus vaccines) and, possibly, the hepatitis B virus vaccine. These patients have therefore been previously exposed to at least one of the T$_h$ epitopes present in pediatric vaccines. Prior exposure to a T$_h$ epitope through immunization with the standard vaccines should establish T$_h$ cell clones which can immediately proliferate upon administration of the synthetic peptide (i.e., a recall response), thereby stimulating rapid B cell responses to Aβ peptides and amyloid deposits.

While the T$_h$ epitopes that may be used in the conjugate with the synthetic peptide of the invention are promiscuous, they are not universal. This characteristic means that the T$_h$ epitopes are reactive in a large segment of an outbred population expressing different MHC antigens (reactive in 50 to 90% of the population), but not in all members of that population. To provide a comprehensive, approaching universal, immune reactivity for the synthetic non-amyloidogenic peptide according to the present invention, a mixture of conjugates with different T$_h$ epitopes cross-linked to a synthetic peptide can be prepared. For example, a combination of four conjugates with promiscuous T$_h$ epitopes from tetanus and pertussis toxins, measles virus F protein and HBsAg may be more effective.

The T$_h$ epitopes in the immunostimulatory peptide cross-linked to the synthetic non-amyloidogenic peptide according to the present invention include hepatitis B surface antigen T helper cell epitopes, pertussis toxin T helper cell epitopes, tetanus toxin T helper cell epitopes, measles virus F protein T helper cell epitope, *Chlamydia trachomitis* major outer membrane protein T helper cell epitopes, diphtheria toxin T helper cell epitopes, *Plasmodium falciparum* circumsporozoite T helper cell epitopes, *Schistosoma mansoni* triose phosphate isomerase T helper cell epitopes, *Escherichia coli* TraT T helper cell epitopes and are disclosed in U.S. Pat. No. 5,843,446, the entire disclosure of which is incorporated herein by reference.

It will be appreciated by those of skill in the art that the term "synthetic" as used with the peptide of the present invention means that it is either chemically synthesized or is produced in an organism only when the host organism is genetically transformed from its native state to produce the peptide. The synthetic peptides of the present invention can be made by synthetic chemical methods which are well known to the ordinary skilled artisan. Accordingly, the synthetic peptides can be synthesized using the automated Merrifield techniques of solid phase synthesis with either t-Boc or F-moc chemistry on Peptide Synthesizers such as an Applied Biosystems Peptide Synthesizer.

Alternatively, longer peptides can be synthesized by well-known recombinant DNA techniques. Any standard manual on DNA technology provides detailed protocols to produce the synthetic peptides of the invention. To construct a nucleotide sequence encoding a synthetic peptide of the present invention, the amino acid sequence is reverse transcribed into a nucleic acid sequence, and preferably using optimized codon usage for the organism in which the peptide will be expressed. Next, a synthetic gene is made, typically by synthesizing overlapping oligonucleotides which encode the peptide and any regulatory elements, if necessary. The synthetic gene is inserted in a suitable cloning vector and recombinant clones are obtained and characterized. The synthetic peptide of the present invention is then expressed under suitable conditions appropriate for the selected expression system and host, and the desired peptide is purified and characterized by standard methods.

An immunostimulatory peptide that can be cross-linked to the synthetic non-amyloidogenic peptide of the invention is also obtainable from the invasin protein of a Yersinia species. The invasins of the pathogenic bacteria Yersinia spp. are outer membrane proteins which mediate entry of the bacteria into mammalian cells (Isberg et al., 1990). Invasion of cultured mammalian cells by the bacterium was demonstrated to require interaction between the Yersinia invasin molecule and several species of the β1 family of integrins present on the cultured cells (Tran Van Nhieu et al., 1991) Since T lymphocytes are rich in β1 integrins (especially activated immune or memory T cells) the effects of invasin on human T cell have been investigated (Brett et al., 1993). It is thought that integrins facilitate the migration of immune T cells out of the blood vessels and through connective tissues to sites of antigenic challenge through their interaction with extracellular matrix proteins including fibronectin, laminin and collagen. The carboxy-terminus of the invasin molecule was found to be co-stimulatory for naive human CD4$_+$ T in the presence of the non-specific mitogen, anti-CD3 antibody, causing marked proliferation and expression of cytokines. The specific invasin domain which interacts with the β1 integrins to cause this stimulation also was identified (Brett et al., 1993). Because of the demonstrated T cell co-stimulatory properties associated with this domain, it can be cross-linked to the synthetic peptide of the present invention to enhance immunogenicity.

Many of the outer membrane proteins of Gram-negative bacteria are both lipid-modified and very immunogenic. Because of the apparent correlation between covalent lipid linkage and immunogenicity, tripalmitoyl-S-glycerine cysteine (Pam$_3$Cys), a lipid common to bacterial membrane proteins, can be coupled to the synthetic peptides in a conjugate to also enhance immunogenicity.

Immunogenicity can further be significantly improved if the synthetic peptides are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses, e.g. to vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum as well.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated-immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

U.S. Pat. No. 4,855,283 teaches glycolipid analogues including N-glycosylamides, N-glycosylureas and N-glycosylcarbamates, each of which is substituted in the sugar residue by an amino acid, as immuno-modulators or adjuvants. U.S. Pat. No. 4,258,029 teaches that octadecyl tyrosine hydrochloride (OTH) functions as an adjuvant when complexed with tetanus toxoid and formalin inactivated type I, II and III poliomyelitis virus vaccine. Also, Nixon-George et al., 1990, reported that octadecyl esters of aromatic amino acids complexed with a recombinant hepatitis B surface antigen enhanced the host immune responses against hepatitis B virus.

The addition of exogenous adjuvant/emulsion formulations which maximize immune responses to Aβ peptides and amyloid deposits are preferred. The adjuvants and carriers that are suitable are those: (1) which have been successfully used in Phase I human trials; (2) based upon their lack of reactogenicity in preclinical safety studies, have potential for approval for use in humans; or (3) have been approved for use in food and companion animals. Some of the adjuvants that are currently undergoing clinical tests are reported in Aguado et al., (1999).

Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher co-glycolide concentrations degrade more rapidly); (2) particle size, (smaller particles degrade more rapidly than larger ones); and, (3) entrapment efficiency, (particles with higher concentrations of entrapped antigen degrade more rapidly than particle with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved. Moreover, delivery of the synthetic peptide according to the present invention entrapped in microparticles can also provide improved efficacy when the microparticulate immunogen is mixed with an exogenous adjuvant/emulsion formulations.

The efficacy of the synthetic peptides can be established and analyzed by injecting an animal, e.g., mice or rats, with the synthetic peptide formulated in alum and then following the immune response to amyloid β peptides.

Another aspect of the present invention provides an immunizing composition which includes an immunizing effective amount of one or more of the synthetic peptides of the invention, or conjugates thereof, and a pharmaceutically acceptable carrier, excipient, diluent, or auxiliary agent, including adjuvants. Accordingly, the synthetic peptides, or conjugates thereof, can be formulated as an immunizing composition using adjuvants, pharmaceutically-acceptable carriers, excipients, diluents, auxiliary agents or other ingredients routinely provided in immunizing compositions. Such formulations are readily determined by one of ordinary skill in the art and include formulations for immediate release and for sustained release, e.g., microencapsulation. The present immunizing compositions can be administered by any convenient route including subcutaneous, oral, intramuscular, or other parenteral or internal route. Similarly the vaccines can be administered as a single dose or divided into multiple doses for administration. Immunization schedules are readily determined by the ordinary skilled artisan. For example, the adjuvants or emulsifiers that can be used in this invention include alum, incomplete Freund's adjuvant, liposyn, saponin, squalene, L121, emulsigen and ISA720. In preferred embodiments, the adjuvants/emulsifiers are alum, incomplete Freund's adjuvant, a combination of liposyn and saponin, a combination of squalene and L121 or a combination of emulsigen and saponin.

The immunizing compositions of the present invention contain an immunoeffective amount of one or more of the synthetic peptides or conjugates thereof and a pharmaceutically acceptable carrier. Such compositions in dosage unit form can contain about 0.5 µg to about 1 mg of each peptide or conjugate per kg body weight. When delivered in multiple doses, the dosage unit form is conveniently divided into the appropriate amounts per dosage.

Immunizing compositions which contain cocktails of two or more of the synthetic peptides, or conjugates thereof, of the present invention enhance immunoefficacy in a broader population and thus provide a better immune response to amyloid β peptides and amyloid deposits. Other immunostimulatory synthetic peptide immunogens are arrived at through modification into lipopeptides so as to provide built-in adjuvanticity for potent vaccines. The immune response to synthetic peptide immunogens of the present invention can be improved by delivery through entrapment in or on biodegradable microparticles of the type described by O'Hagan et al (1991). The immunogens can be encapsulated with or without adjuvant, including covalently attached lipid moiety such as $Pam_3Cys$, and such microparticles can be administered with an immunostimulatory adjuvant such as Freund's Incomplete Adjuvant or alum. The microparticles function to potentiate immune responses to an immunogen and to provide time-controlled release for sustained or periodic responses. for oral administration, and for topical administration (O'Hagan et al., 1991).

A further aspect of the present invention is a method for immunization with the synthetic peptide or conjugate thereof of the present invention. This method according to the present invention involves administering to a mammal, in need thereof, preferably human, an immunizing composition containing the synthetic peptide(s) or conjugates thereof. Efficacy will be tested first in transgenic mouse models of AD such as the mouse model used in Schenk et al. (1999) or other publicly or commercially available AD transgenic mouse model.

Yet another aspect of the present invention provides for antibodies raised against the immunogenic peptides of the present invention and molecules which includes the antigen-binding portion of such antibodies.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al., (1990) and Gross et al., (1989)). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$–$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al., (1975); U.S. Pat. No. 4,376,110; Harlow et al., (1988); and Colligan et al., (1993), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al., 1984; Morrison et al., 1984; Boulianne et al., 1984; Cabilly et al., 1984; Neuberger et al., 1985; Taniguchi et al., 1985; Morrison et al., 1986; Neuberger et al., 1986; Kudo et al., 1986; Morrison et al., 1986; Sahagan et al., 1986; Robinson et al., 1987; Liu et al., 1987; Sun et al., 1987; Better et al., 1988; and Harlow et al., 1988. These references are hereby incorporated herein by reference.

A "molecule which includes the antigen-binding portion of an antibody," is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The present invention also provides a pharmaceutical composition containing a molecule which includes the antigen-binding portion of an antibody raised against a peptide of the present invention, and a pharmaceutically acceptable, carrier, diluent, excipient or auxiliary agent. The formulation of pharmaceutical compositions, which formulation is conventionally used in a highly skilled art and which compositions are suitable for its intended use as a therapeutic for reducing the formulation of amyloid fibrils and deposits, can be developed with only routine experimentation by those of skill in the art.

According to the present invention, the molecule which includes the antigen-binding portion of an antibody raised against the immunogenic peptides of the present invention can be administered to a subject in need thereof to reduce the formation of amyloid fibrils and deposits. The site of administration, the dosage, and the schedule of administration are determined according to well-established procedures used by those of skill in the art.

Having now generally described the invention, the same will be more readily understood through reference to the following examples which are provided by way of illustration and is not intended to be limiting of the present invention.

EXAMPLE 1

The experiments in this example demonstrate that immunization in transgenic APP mice (Tg2576) for 7 months with a non-amyloidogenic, non-toxic Aβ homologous peptide reduced cortical and hippocampal brain amyloid burden by 89% (p=0.0002) and 81% (p=0.0001), respectively. Concurrently, brain levels of soluble Aβ1-42 were reduced by 57% (p=0.0019). Ramified microglia expressing interleukin-1β associated with the Aβ plaques were absent in the immunized mice indicating reduced inflammation in these animals. The materials and methods used in the experiments in this example and the experimental results are presented below.

MATERIALS AND METHODS
Peptides

The peptides used (Aβ1-40, Aβ1-42, Aβ1-30-NH$_2$(SEQ ID NO:1), and K6Aβ1-30-NH$_2$ (SEQ ID NO NO:6)) were synthesized at the Keck Foundation (Yale University, New Haven, Conn.), as described previously (Sigurdsson et al., 2000). Non-amyloidogenic peptides according to the present invention are synthesized using solid-phase tBOC (N-tert-butyloxycarbonyl) chemistry, purified by HPLC, and characterized by HPLC and laser desorption mass spectroscopy.

The peptide used for the immunizations, K6Aβ1-30-NH$_2$, maintains the two major immunogenic sites of Aβ peptides, which are residues 1–11 and 22–28 of Aβ1-42 based on the antigenic index of Jameson et al. (1998), and on preliminary results obtained in the laboratory of the present inventors.

The Aβ1-30-NH$_2$ and K6Aβ1-30-NH$_2$ peptides were amidated at the C-terminus to further preserve their antigenicity.

Secondary Structure Studies

Secondary structure (α-helix, β-sheet, and random coil) of the peptides was evaluated by circular dichroism (CD) as described previously (Soto et al., 1998 and Soto et al., 1996). Results are expressed as molar ellipticity in units of deg cm$^2$ dmol$^{-1}$, and the data was analyzed by the Lincomb and CCA algorithms (Perczel et al., 1992) to obtain the percentages of different types of secondary structure.

While the secondary structure of the synthesized peptides was evaluated by circular dichroism (CD), it can also be evaluated by Fourier-Transform InfraRed spectroscopy (FTIR), using published protocols from Aucouturier et al. (1999). Although CD is sensitive to backbone conformation and FTIR is sensitive to the degree and strength of hydrogen bonding of amide groups (which is dependent of the structure), these two techniques ultimately give similar information: the percentages of different secondary structure motifs, i.e., α-helix, β-sheet, β-turn and random coil (Surewicz et al., 1993). CD is a very well-established technique for studying the secondary structure of proteins and peptides in solution, giving fairly accurate estimations of the content of different structural motifs. A major advantage of FTIR spectroscopy for structural characterization is the lack of dependence on the physical state of the sample. Samples may be examined as aqueous or organic solutions, hydrated films, inhomogeneous dispersions, aggregated materials or even proteins in solid state. Therefore, CD and FTIR are complementary for studying the secondary structure of peptides.

The experimental procedure for circular dichroism is performed according to Golabek et al., (1996) and Soto et al. (1996 and 1998) as follows: CD spectra of solutions containing synthetic peptides (1–5 μM in 300 μl of 10 mM sodium phosphate, pH 7.2) is recorded in a Jasco J-720 spectropolarimeter at 25° C. using a 0.1 cm path-length cell with double distilled, deionized water and TFE (spectroscopy grade) being used as solvents. Calibration of the instrument is performed with an aqueous solution of d-(+)-10-camphorsulfonic acid. Spectra is recorded at 1 nm intervals over the wavelength range 180 to 260 nm and buffer spectra obtained under identical conditions is subtracted.

The experimental procedure for Fourier-Transform Infra-Red Spectroscopy according to Aucouturier et al. (1999) is as follows: Solutions or suspensions containing soluble or aggregated synthetic peptides (5–10 mg/ml) will be prepared in H$_2$O and D$_2$O buffers at neutral pH, and 10 μl will be loaded into an infrared cell with CaF$_2$ plates and 6 μm path-length spacer. Spectra will be recorded with a Perkin Elmer model 2000 FTIR spectrophotometer at 25° C., as described (Aucouturier et al., 1999; Soto et al., 1995). For each spectrum, 1000 scans will be collected in the single-beam mode with 2 cm$^{-1}$ resolution and a 1 cm$^{-1}$ interval from 4000 to 1000 cm$^{-1}$. Smoothing and Fourier self-deconvolution will be applied to increase the spectral resolution in the amide I region (1700–1600 cm$^{-1}$) and the iterative fitting to Lorentzian line shapes will be carried out to estimate the proportion of each secondary structural element.

Studies of Amyloid Fibril Formation in Vitro

Studies of amyloid fibril formation in vitro can be performed using published protocols from the laboratory of the present inventors (Castano et al., 1995; Wisniewski et al., 1991; Wisniewski et al., 1993 and Wisniewski et al., 1994). Aliquots of the synthetic peptides at a concentration ranging between 25–250 μM, prepared in 0.1M Tris, pH 7.4, can be incubated for different times, and their fibril formation compared to that of Aβ1-28, Aβ1-40 and Aβ1-42. In this example, aliquots of the peptides prepared in 0.1M Tris, pH 7.4, were incubated for different times, and their fibril formation compared to that of Aβ1-30-NH$_2$ and Aβ1-42. In vitro fibrillogenesis was evaluated by a fluorometric assay based on the fluorescence emission by thioflavine T, as previously described by the laboratory of the present inventors (Soto et al., 1998 and Jameson et al., 1998). Thioflavine T binds specifically to amyloid and this binding procedures a shift in its emission spectrum and a fluorescent enhancement proportional to the amount of amyloid formed (LeVine et al. 1993).

Although not performed in this example, in vitro fibrillogenesis can also be evaluated by three other different methods:

(A) A spectrophotometric assay based on the specific interaction of Congo red with amyloid fibrils. After the incubation period, 2 μl of Congo red (1.5 mg/ml) will be added to each sample and incubated in the dark for 1 h. The samples will then be centrifuged at 15,000 rpm for 10 min and the absorbance of the supernatant measured at 490 nm. The amount of amyloid formed is directly proportional to the decrease in the supernatant absorbance (Castano et al., 1986).

(B) A sedimentation assay will be used as described (Soto et al., 1995). Briefly, samples will be centrifuged at 15,000 rpm for 10 min to separate the soluble and aggregated peptide. The amount of material in solution will be analyzed by microbore HPLC using a reverse phase Vydac C4 column and a linear gradient of 3–70% acetonitrile. The percentage of aggregated peptide will be estimated by comparing the area of the peak corresponding to the soluble peptide in each incubated sample with an identical control of non-incubated sample.

(C) Additional characterization of fibrillogenesis will be performed by Congo red staining and electron microscopic examination after negative staining (Castano et al., 1995; Wisniewsi et al., 1991; Wisniewski et al., 1993 and Wisniewski et al., 1994). For electron microscopy, the incubated samples of peptides will be placed on carbon formar-coated 300-mesh nickel grids and stained for 60 seconds with 2% uranyl acetate under a vapor of 2% glutaraldehyde. Grids will be visualized on a Zeiss EM 10 electron microscope at 80 kV. For Congo red staining, the incubated peptides will be placed onto gelatin-coated glass microscope slides and air-dried at 37° C. The slices will then be immersed in 0.2% Congo red dissolved in 80% aqueous ethanol saturated with NaCl for 60 min at room temperature, washed three times with water and visualized by polarized light microscopy.

Neurotoxicity

The potential neurotoxicity of K6Aβ1-30-NH$_2$ (1–100 μM) was evaluated at 2 and 6 days in a human neuroblastoma cell line (SK-N-SH) using the standard MTT assay as described by the manufacturer (Roche Molecular Biochemicals, Indianapolis, Ind.). Aβ1-30-NH$_2$, Aβ1-40 and Aβ1-42 were used as control peptides. Briefly, cells were plated at 10,000 cells/100 μl culture medium per well in flat bottom, 96 well microtiter plates. The cells were allowed to attach to the plate overnight in an incubator (37° C., 5.0% CO$_2$), and then 10 μl of freshly prepared peptide solution (in nanopure H$_2$O) was added. Aβ1-42 was only partially soluble at 100 μM and was, therefore, added as a suspension at that concentration. Subsequent steps were as described in the assay protocol.

Animals

The vaccination was performed in the Tg2576 APP mouse model developed by Karen Hsiao et al. (1996). These mice develop Aβ plaques as early as at 11–13 months of age. This model was chosen over the double Tg APP/PS1 model (Holcomb et al., 1998) because the age of onset and progression of Aβ deposition in the single Tg APP mice more closely resembles that of AD. Age-matched vehicle-treated Tg mice and non-Tg littermates receiving K6Aβ1-30-NH$_2$ were used as controls, and the animals received their first injection at 11–13 months, at which time few plaques should already be present. Four mice were in each group. The animals were maintained on a 12 h light-dark cycle, and had access to food and water ad libitum. The animal care was in accordance with institutional guidelines.

Vaccine Administration: K6Aβ1-30-NH$_2$ was supplied as trifluoroacetic acid (TFA) salt. The immunization procedure was performed as previously described by Schenk et al. (1999) except that the peptide was not incubated overnight at 37° C. before injection. Briefly, the peptide was dissolved in PBS at a concentration of 2 mg/ml and then mixed 1:1 (v/v) with the adjuvant or PBS. Complete Freund's adjuvant was used for the first injection, incomplete Freund's adjuvant for the next 3 injections, and PBS from the 5$^{th}$ injection forward. The mice received a subcutaneous injection of 100 μl of the mixture (i.e., 100 μg/100 μl) followed by a second injection two weeks later, and then monthly thereafter.

Antibody Titers: Antibody titers were determined by serial dilutions of sera using an ELISA assay as described previously (Jimenez-Huete et al., 1998), where Aβ or its derivative is coated onto microtiter wells. The titer, defined as the dilution yielding 50% of the maximum signal, was detected by a goat anti-mouse IgG linked to a horseradish peroxidase (Amersham Pharmacia Biotech, Piscataway, N.J.), and tetramethyl benzidine (Pierce, Rockford, Ill.) was the substrate.

Histology: Mice were anesthetized with sodium pentobarbital (150 mg/kg, i.p.), perfused transaortically with phosphate buffer and the brains processed as previously described (Sigurdsson et al., 1996). The right hemisphere was immersion fixed in periodate-lysine-paraformaldehyde, whereas the left hemisphere was snap frozen for measurements of Aβ levels using established ELISA methods (Mehta et al., 1998 and Mehta et al., 2000). Serial coronal sections (40 μm) were cut and five series of sections at 0.2 mm intervals were saved for histological analysis of 1) 6E10, 2) Congo red, 3) Interleukin-1β/OX42/tomato lectin, 4) GFAP, and 5) cresyl violet stained sections. 6E10 recognizes Aβ and stains both pre-amyloid and Aβ plaques (Kim et al., 1990). Congo red staining was performed to identify amyloid lesions in these animals. GFAP is a component of the glial intermediate filaments that form part of the cytoskeleton and is found predominantly in astrocytes. Microglia appear to be the major source of interleukin-1 (IL-1) within the CNS (Schobitz et al., 1994), and OX-42 recognizes CD11b on microglia, a rat equivalent of the human C3bi receptor (Robinson et al., 1986). Tomato lectin binds to poly-N acetyl lactosamine residues and has in neural tissue specific affinity for microglial cells (Acarin et al., 1994). Both astrocytes and microglia are associated with Aβ deposits. Staining with cresyl violet was performed to determine if the immunization was causing neuronal shrinkage and/or cell loss in these animals. Following sectioning, the series were placed in ethylene glycol cryoprotectant and stored at −20° C. until used.

Cresyl violet and Congo red: Mounted sections were defatted in xylene and hydrated in a gradient of ethyl alcohol and water series. Staining was performed as previously described (Sigurdsson et al., 1996 and 1997 and Soto et al., 1998)

6E10, GFAP, IL-1β and OX-42: Staining was performed as previously described (Sigurdsson et al., 1996 and Soto et al., 1998). Briefly, sections were incubated in 6E10 (kindly provided by Richard Kascsak, Institute for Basic Research) primary antibody that selectively binds to human Aβ at a 1:1000 dilution. A mouse on mouse immunodetection kit (Vector Laboratories, Burlingame, Calif.) was used where the anti-mouse IgG secondary antibody was used at a 1:2000 dilution. GFAP (1:500; Dako, Denmark), IL-1β (1:250; Endogen, Rockford, Ill.) and OX-42 (1:250; Biosource Int., Camarillo, Calif.) staining was performed the same way as the 6E10 staining, except the secondary antibody was diluted 1:1300. The sections were reacted in 3,3'-diaminobenzidine tetrahydrochloride (DAB) with or without nickel ammonium sulfate (Ni) intensification. For double labeling of IL-1β and Aβ plaques, sections were first stained for IL-1β (DAB/Ni; black) where peroxidase was the enzyme. The plaques (6E10) were then stained using the Vector Red Alkaline Phosphatase Substrate Kit I (Vector).

Tomato Lectin: Sections removed from the cryoprotectant were washed in PBS, 0.3% Triton-X-100 in PBS (PBS-Tx) and then incubated for 30 minutes in 0.3% hydrogen peroxide in PBS to quench endogenous peroxidase activity. Following 2 hours incubation with tomato lectin (10 μg/ml PBS; Vector), sections were washed in PBS-Tx and then reacted with avidin-horseradish peroxidase (Vector) for one hour. Subsequent steps were as those used for the antibody staining.

Image Analysis: Immunohistochemistry of tissue sections was quantified with a Bioquant image analysis system, and unbiased sampling was used (West et al., 1999). All procedures were performed by an individual blind to the experimental condition of the study. Cortical area analyzed was dorsomedially from the cingulate cortex and extended ventrolaterally to the rhinal fissure within the right hemisphere. The area of the grid was 800×800 $\mu m^2$ and amyloid load was measured in 10 frames per mouse (each: 640×480 $\mu m^2$), chosen randomly. Hippocampal measurements were performed on the entire hippocampus in a similar manner as the cortical analysis. The Aβ burden is defined as the percent of area in the measurement field occupied by reaction product.

Sandwich ELISA Assay for Soluble Aβ Levels: Prior to extraction of Aβ from brain tissue, 10% (w/v) homogenates were prepared in tissue homogenization buffer (20 mM Tris pH 7.4, 250 mM sucrose, 1 mM EDTA, 1 mM EGTA). Immediately before use, 1/100 volume of 100 mM phenylmethylsulfonyl fluoride stock solution (in ethanol) and 1/1000 volume of LAP (5 mg each of leupeptin, antipain and pepstatin Aβ per ml of N-N-dimethylformamide) were added to the homogenization buffer. The homogenate was then thoroughly mixed with an equal volume of 0.4% diethylamine/100 mM NaCl, then spun at 135,000×g for one hour at 4° C., and subsequently neutralized with 1/10 volume 0.5 M Tris, pH 6.8. The samples were then aliquoted, flash frozen on dry ice, and stored at −80° C. until loaded onto plates. Soluble Aβ levels were measured in the left hemisphere using monoclonal antibody 6E10 (specific to an epitope present on 1–16 amino acid residues of Ad), rabbit antiserum R162 (specific for Aβ40) and rabbit antiserum 165 (specific for Aβ42) in a double antibody sandwich ELISA as described previously (Mehta et al., 1998 and 2000). The optical density (OD) was measured at 450 nm in a microELISA reader. The relationship between OD and Aβ40 or Aβ42 concentrations was determined by a four-parameter logistic log function. Nonlinear curve fitting was performed with KlinetiCalc program (Biotek Instruments, Inc. Winooski, Vt.) to convert OD of plasma to estimated concentrations. All samples were coded, and the investigators were blinded to group assignment until levels were measured and recorded. The detection limit of the assay is 10 pg/ml for Aβ40 and Aβ42. The percent coefficient of variation normally ranges from 8 to 14% (inter-assay) and 10 to 18% (intra-assay).

Data Analysis: The cell culture data was analyzed by one-way ANOVA, followed by a Dunnett's test for post hoc analysis (GraphPad Prism 3.0). An unbiased stereological image analysis system (Bioquant, R&M Biometrics Inc., Nashville, Tenn.) was used to determine the amyloid burden in 6E10 stained brain sections. The data for the amyloid burden and the levels of soluble Aβ within the brain were analyzed by a Student's t-test, two-tailed.

RESULTS

Before conducting the vaccination study it was necessary to confirm that the prototype peptide, KKKKKK-Aβ1-30-NH$_2$, had indeed less β-sheet structure, reduced fibrillogenicity compared to Aβ1-42, and that it was non-toxic in neuronal culture. The secondary structure of these peptides was determined by circular dichroism (CD), and their ability to form amyloid fibrils by a thioflavin-T fluorometric assay. An additional control peptide was Aβ1-30-NH$_2$.

CD Assay: Compounds with high β-sheet content are more toxic and more likely to form fibrils than compounds with low β-sheet content (Pike et al., 1991). The peptide with the polylysine at the N-terminus had much less β-sheet content that the amidated Aβ1-30 or Aβ1-42 (Table 1).

The (K)$_6$-Aβ1-30-NH$_2$ peptide also does not form fibrils following incubation at 37° C. for at least 15 days. This data clearly shows that the addition of polylysine at the N-terminus alters the peptide so that the β-sheet content is much lower then either Aβ1-42 or Aβ1-30. In addition, the β-sheet content of the (K)$_6$-Aβ1-30-NH$_2$ peptide does not increase with time. The β-sheet content of Aβ1-42 increased to 55% after 96 hr., while that of (K)$_6$-Aβ1-30-NH$_2$ stayed at 16–18%.

TABLE 1

| Time | Aβ1-42 | | | Aβ1-30-NH$_2$ | | | (K)$_6$-Aβ1-30-NH$_2$ | | |
| --- | --- | --- | --- | --- | --- | --- | --- | --- | --- |
| (hr) | alpha | beta-sheet | random | alpha | beta-sheet | random | alpha | beta-sheet | random |
| 0 | 9 | 36 | 55 | 5 | 37 | 58 | 2 | 18 | 79 |
| 24 | 9 | 40 | 51 | 8 | 36 | 56 | 5 | 16 | 78 |
| 96 | 5 | 55 | 40 | 7 | 49 | 44 | 34 | 16 | 50 |

Thioflavin T assay: Aβ1-42 was already fibrillar at t=0, whereas Aβ1-30-NH$_2$ gradually formed fibrils over time (FIG. 1). The relatively high degree of thioflavin T staining of the Aβ1-30-NH$_2$ versus Aβ1-42 after 6 days reflects the known batch-to-batch variability of Aβ peptide fibril formation (Soto et al., 1995), as well as some degree of pellet formation by the Aβ1-42 with prolonged incubation. K6Aβ1-30-NH$_2$ did not form fibrils following incubation at 37° C. for at least 15 days.

Figure 2A:
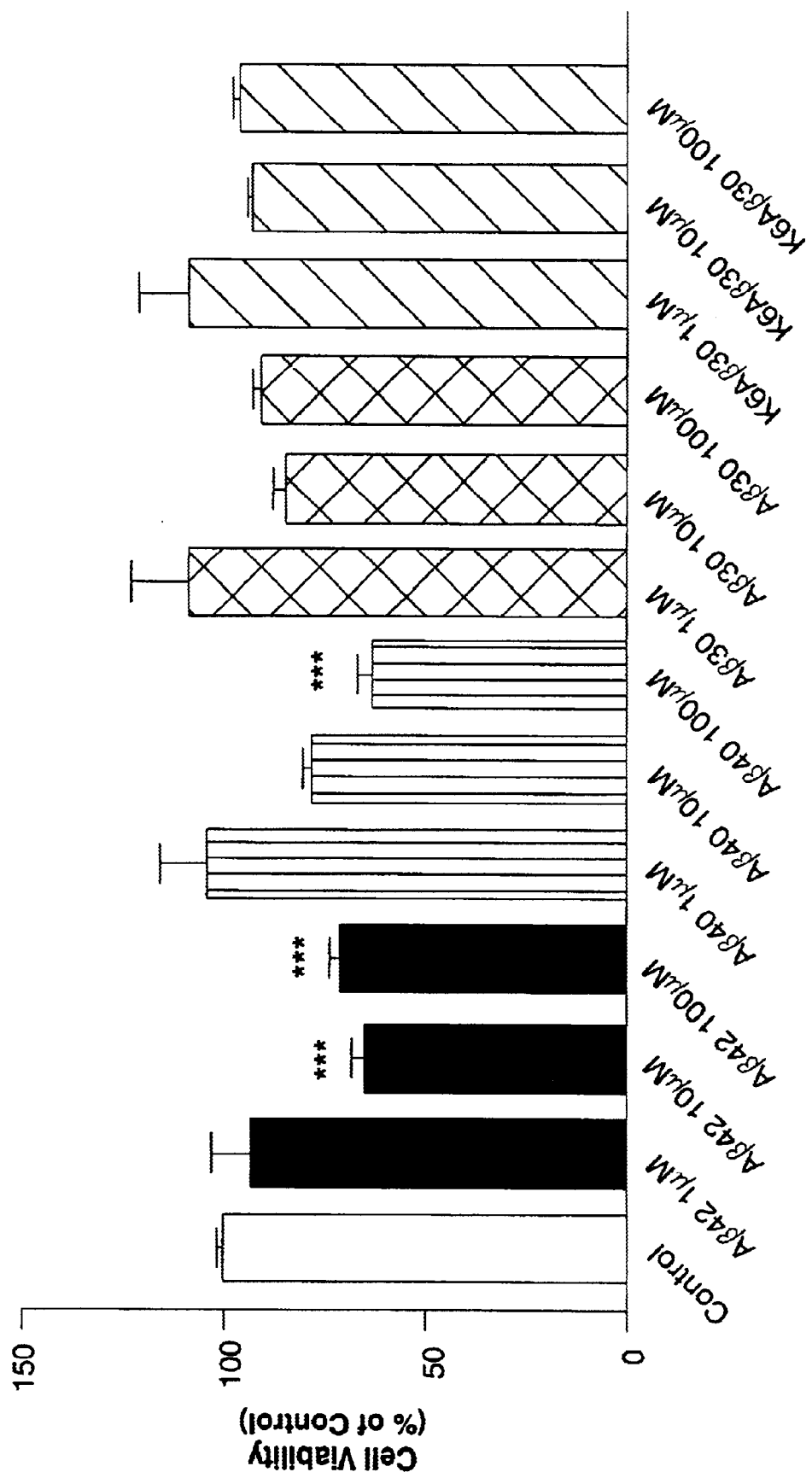
FIGS. 2A and 2B show that Aβ40 and Aβ42 are toxic to human neuroblastoma cells (SK-N-SH) in culture as determined by the MTT assay, whereas K6Aβ30-NH$_2$ has no effect at 2 days (FIG. 2A) and is slightly trophic at 6 days (FIG. 2B). *p<0.05; p<0.01; *p<0.001 compared to VEH group (one-way ANOVA).
Figure 2B:
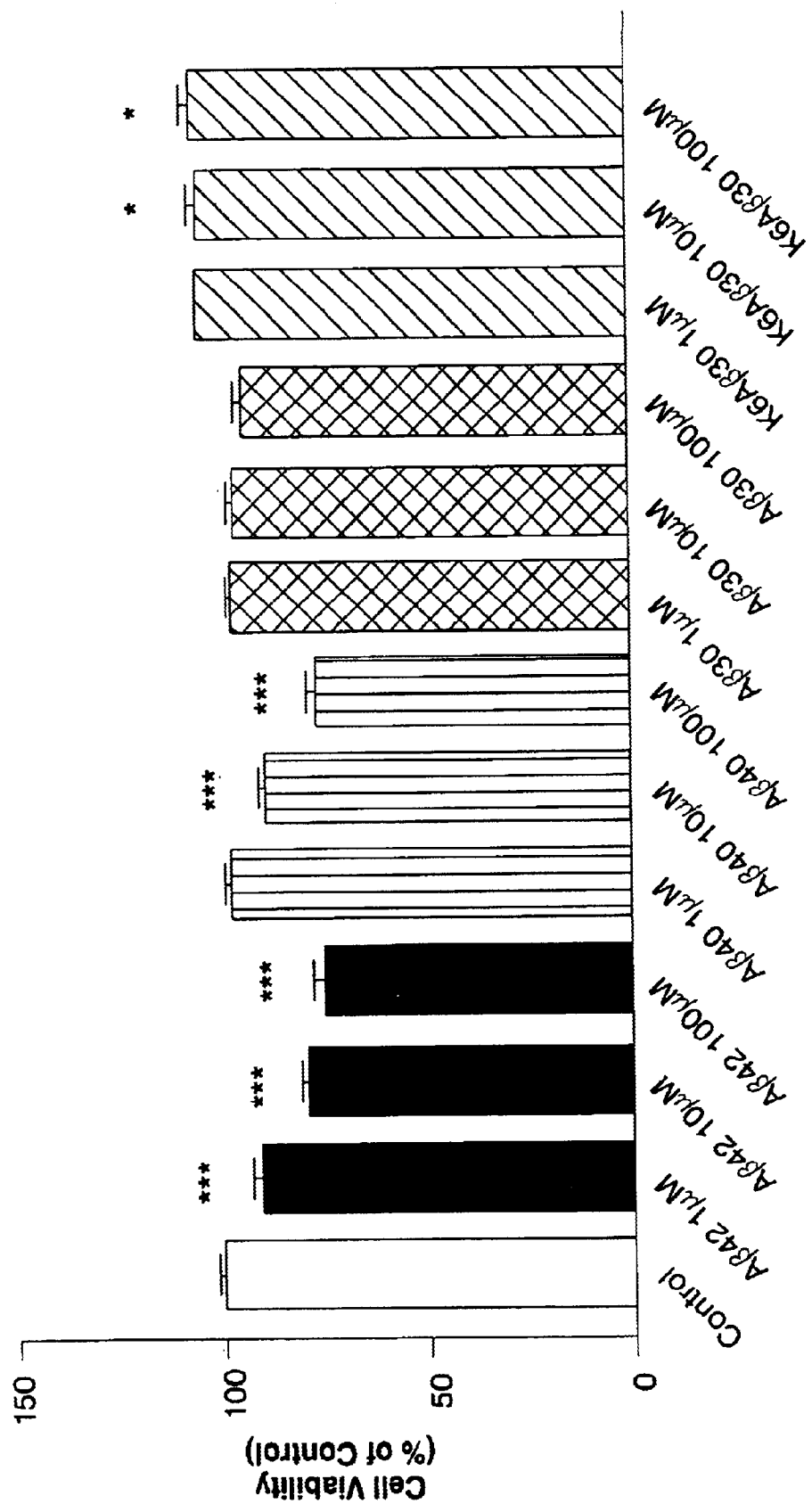

Neurotoxicity: To further assess the safety of this vaccination approach the neurotoxicity of K6Aβ1-30-NH$_2$ was determined. K6Aβ1-30-NH$_2$ had no effect on cell viability at 2 days and was slightly trophic at 6 days (p<0.05), whereas Aβ1-40 and Aβ1-42 were toxic (p<0.05–0.001) to the human neuroblastoma cells (SK-N-SH), compared to vehicle group, as determined by the MTT assay (FIG. 2A and B). During the incubation period, aggregates were visible under the microscope only in culture wells containing Aβ1-42 (10–100 μM).

Antibody Titer: Tg2576 and their non-Tg littermates were vaccinated with K6Aβ1-30-NH$_2$ or vehicle. Almost all the mice developed antibodies against the immunogen (K6Aβ1-30-NH$_2$), that cross-reacted with Aβ1-40 and Aβ1-42. The titer, defined as the dilution yielding 50% of the maximum signal, ranged from a few hundreds to several thousands (data not shown). Vehicle treated animals injected with the adjuvant and PBS did not develop antibodies against these three peptides (data not shown). Non-transgenic mice had generally higher titer against all 3 peptides, and the polyclonal antibodies had higher avidity for the immunogen compared to Aβ1-40 and Aβ1-42. These findings are as expected because the immunogen is based on the human sequence of Aβ which differs in 3 amino acids from the mouse Aβ (Johnstone et al., 1991), and K6Aβ1-30-NH$_2$ that elicited the immune response should have more binding motifs for antibodies than the intact Aβ peptides.

Figure 3A:
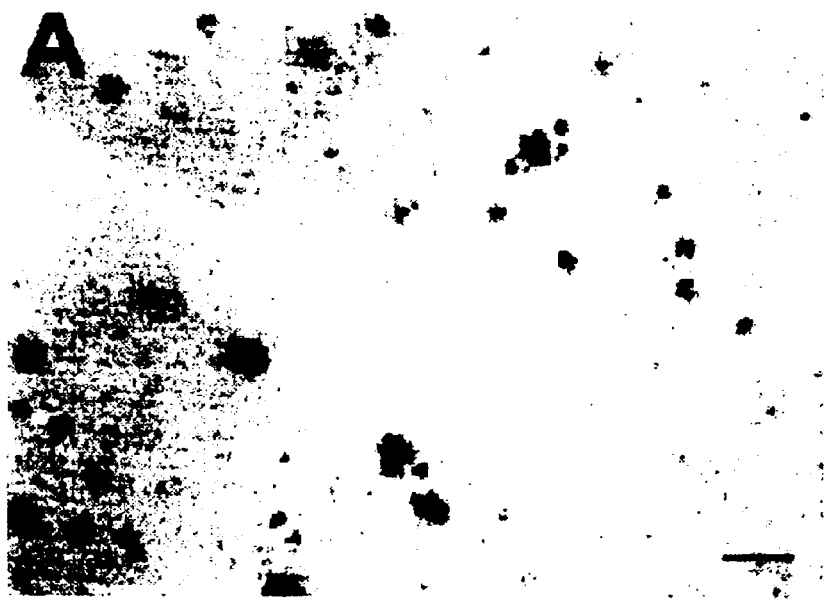
FIGS. 3A–3D show coronal sections (X50; original magnification) stained with 6E10 against Aβ, through the hippocampus and cortex in a Tg control-(FIG. 3A) and K6Aβ1-30-treated (FIG. 3B) Tg mouse.
Figure 3B:
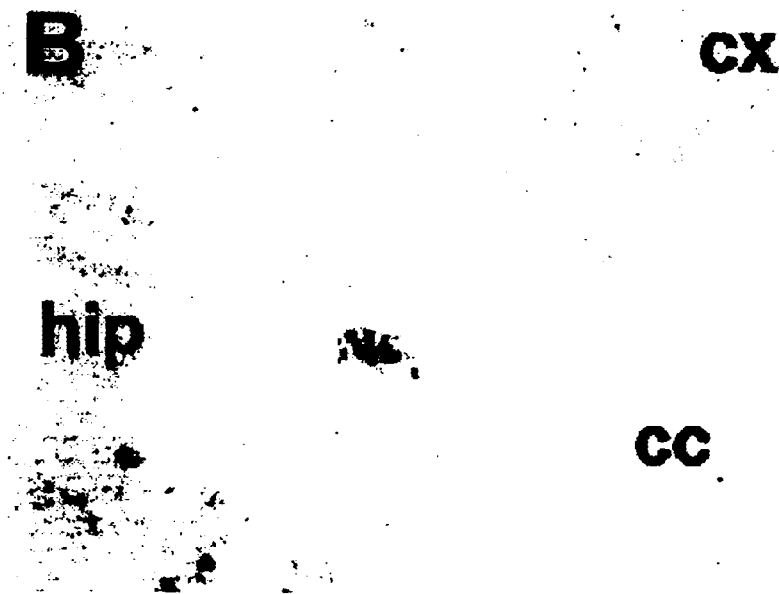
Figure 3C:
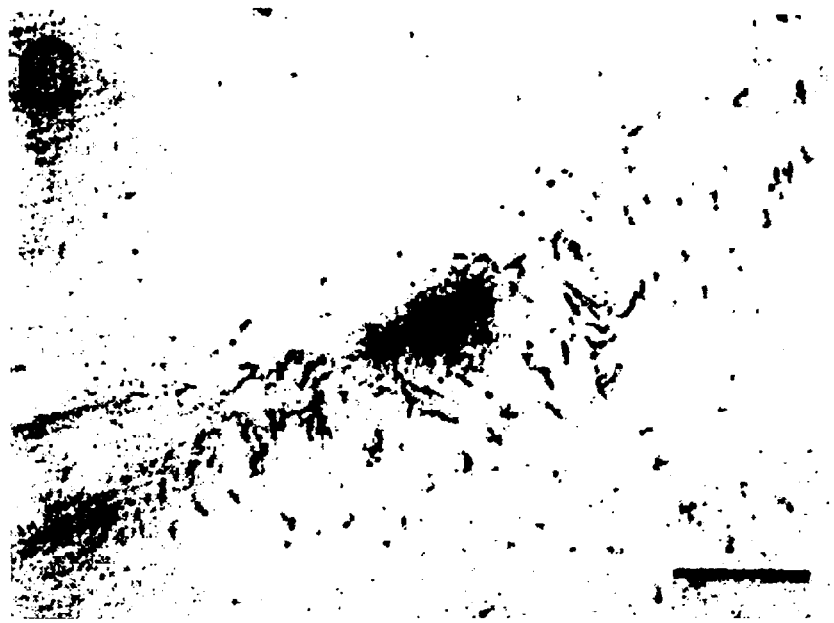
Figure 3D:
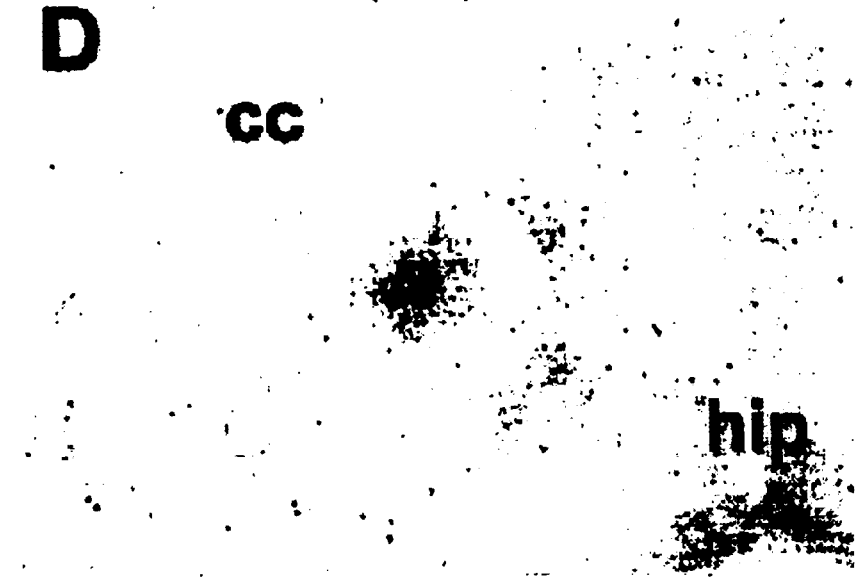

Amyloid Burden and Associated Histopathology: The mice were killed at 18–20 months of age after 7 months treatment, and their right hemisphere was processed for histology as described (Sigurdsson et al., 1996). The brain sections were stained with cresyl violet, Congo red, tomato lectin and with antibodies against: 1) human Aβ (6E10); microglia (OX-42; IL-1β); and GFAP (anti-GFAP). Following K6Aβ1-30-NH$_2$ vaccination, cortical and hippocampal amyloid burden in the Tg mice was reduced by 89% and 81%, respectively (FIGS. 3A, 3B; 4A, 4B), as determined by stereological techniques. The total number of Congo red positive amyloid deposits was reduced in the immunized animals; however, the percentage of Aβ-immunoreactive lesions that were Congo red positive appeared to remain the same as in the non-immunized Tg mice. The clearance of the amyloid deposits appeared to be similar in other brain regions. Selected brain sections from a control mouse with high amyloid burden and an immunized mouse with reduced amyloid burden were stained with sera from several immunized and control mice, whose antibody titer ranged from zero to three thousand. As expected, with increasing titer more plaques were stained and the pattern was similar in both mice (data not shown). There was no obvious difference between the Tg treatment groups in cresyl violet staining. Reactive astrocytes were observed associated with all amyloid plaques. Since the vehicle-treated Tg mice had a higher plaque burden, they had more clusters of astrocytes than immunized Tg mice. OX-42 staining of ramified rather than phagocytic (ameboid) microglia was predominantly observed associated with plaques. To verify that this lack of microglial phagocytes was not due to downregulation of the CD11b receptor, the binding motif of OX-42 (Robinson et al., 1986), sections from all treatment groups were stained with tomato lectin. This particular lectin binds to poly-N-acetyl lactosamine residues found predominantly in ramified and phagocytic microglial cells, in addition to endothelial- and ependymal cells (Acarin et al., 1994). These two latter cell types were stained in all the mice. The microglial lectin staining resembled the OX-42 staining. In other words, in both immunized and control Tg groups, the microglia did not have phagocytic morphology and number of ramified microglial processes per plaque appeared to be similar between immunized and non-immunized mice (data not shown). On the other hand, IL-1β staining of ramified microglial cells was prominent surrounding the Aβ plaques in the control Tg mice (FIG. 3C), whereas virtually no IL-1β staining was observed in the immunized mice (FIG. 3D). Significantly, there was no indication of glomerulonephritis in hemotoxylin/eosin stained kidney sections from the K6Aβ1-30-NH$_2$ treated mice, suggesting that the mice had not developed an autoimmune disorder.

Figure 4A:
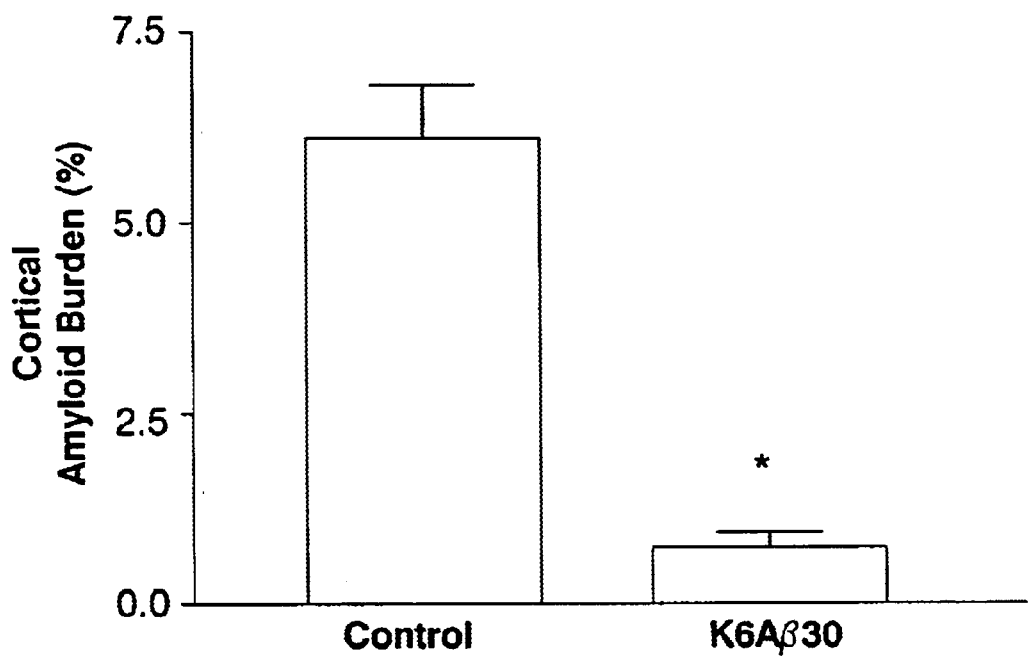
FIGS. 4A–4C show the reduction in cortical (FIG. 4A) and hippocampal (FIG. 4B) amyloid burden (6E10) following 7 months treatment with K6Aβ1-30-NH$_2$. There is an 89% reduction in cortical amyloid burden (*p=0.0002; t-test; n=4 per group) and an 81% reduction in hippocampal amyloid burden (*p=0.0001). Soluble Aβ1-42 levels (FIG. 4C) are reduced by 57% within the brains of the vaccinated mice (*p=0.0019).
Figure 4B:
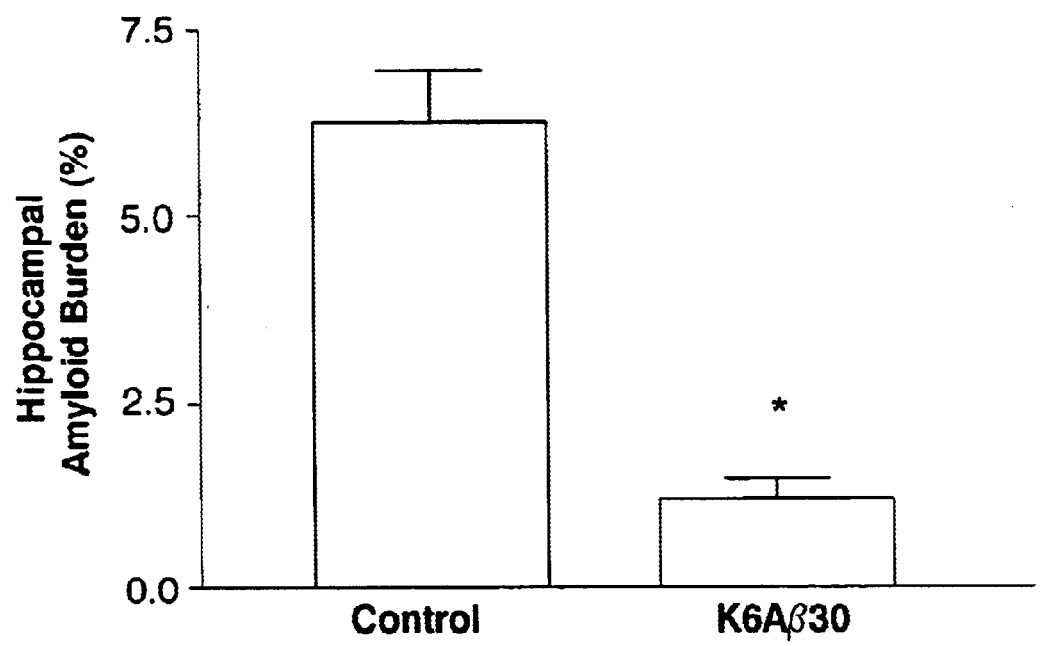
Figure 4C:
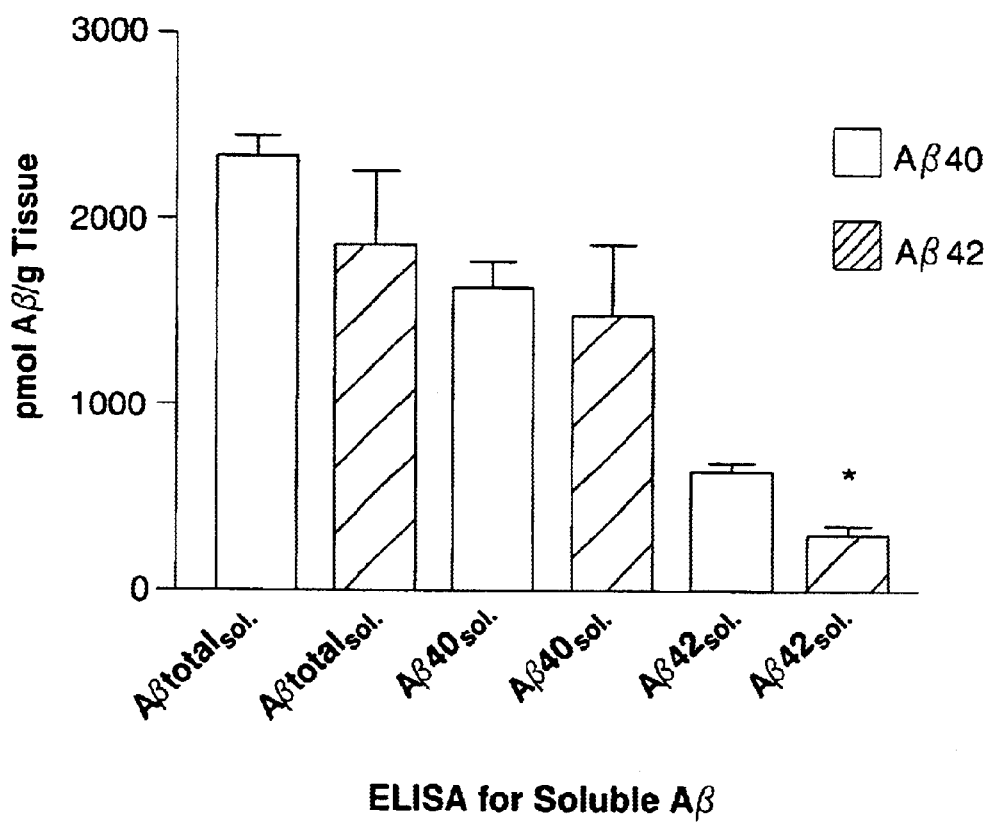

Soluble Aβ by ELISA: Measurements of soluble Aβ levels were performed on the left hemisphere of the mice whose right hemisphere was used for histology. Soluble Aβ1-42 was reduced by 57% following vaccination with K6Aβ1-30-NH$_2$ for 7 months (p=0.0019), compared to control group (FIG. 4C). Although there was a trend for reduced levels of soluble total Aβ and Aβ1-40 in the K6Aβ1-30 treated group, the values were not significantly different from the vehicle group.

Overall, immunization in Tg APP mice with non-amyloidogenic/non toxic (low β-sheet content) Aβ homologous peptide results in a similar reduction of amyloid burden as observed by Schenk et al. (1999) where they used a fibrillar/toxic (high β-sheet content) Aβ1-42.

DISCUSSION

These findings demonstrate that Aβ aggregates/fibrils are not necessary to elicit a sufficient immune response that results in clearance of Aβ plaques. The use of non-fibrillar/non-toxic Aβ homologous peptides, such as K6Aβ1-30-NH$_2$, is a safer vaccination approach for humans.

The mechanism of the vaccination-induced reduction in cerebral amyloid burden is not fully understood. However, based on the passive vaccination study by Bard et al. (2000) it is likely that antibodies have a pivotal role. Interestingly, they demonstrated that there was no correlation between antibody efficacy and affinity for soluble Aβ or binding to aggregated synthetic Aβ peptide. Effective antibodies were, however, able to bind to plaques in unfixed brain sections. Janus et al. (2000), using the same protocol as Schenk et al. (1999) observed that the sera from Aβ-immunized mice preferentially stained dense core plaques rather than diffuse Aβ deposits suggesting that the antibodies may have a higher affinity for β-sheet Aβ. Based on these somewhat contradictory findings, more studies are needed on Aβ-antibody interactions that may give insight into the mechanism of antibody-mediated Aβ clearance. It is unlikely that these antibodies are affecting the production of Aβ because they do not recognize APP (Weiner et al., 2000). It is more probable that the antibodies enhance clearance of Aβ through microglial activation following antibody binding to Aβ plaques (Schenk et al., 1999 and Bard et al., 2000). Their effect may also in part be due to binding to soluble Aβ within the brain, that alters the equilibrium between deposited Aβ vs. soluble Aβ. Given the numerous reports that show that Aβ can bi-directionally cross the blood brain barrier (Zlokovic et al., 1993; Maness et al., 1994; Martel et al., 1996; Poduslo et al., 1997 and 1999; Mackic et al., 1998; Shibata et al., 2000 and Ji et al., 2001) the vaccination effect may be in part mediated through binding of the antibodies to soluble Aβ in peripheral fluids. Subsequent reduction in peripheral Aβ levels may alter the equilibrium between Aβ found within and outside the CNS that may result in efflux of Aβ out of the CNS. A recent report shows that in the Tg2576 mice, plasma levels of Aβ decrease as cerebral plaque burden increases (Kawarabayashi et al., 2001). This suggests an interaction between these two compartments that can be manipulated.

Interestingly, in the behavioral vaccination study by Morgan et al. (2000), they observed a partial reversal in cognitive deficits in APP/PS1 mice although cerebral amyloid burden as measured by immunohistochemistry was not significantly reduced. As pointed out by Morgan et al. (2000), soluble Aβ has been proposed to cause synapse loss in APP Tg mice, as some Tg lines have reduced synaptophysin staining in the dentate gyrus without Aβ deposits (Mucke et al., 2000). Therefore, a possible explanation for the cognitive improvement in the immunized mice in the absence of reduced plaque burden, was a decrease in soluble Aβ, although this potential connection was not measured in their study (Morgan et al., 2000). The results obtained in the laboratory of the present inventors show that following 7 months treatment, the 81–89% reduction in amyloid plaque burden is associated with a 57% reduction in soluble Aβ1-42 within the brain, whereas the reduction in soluble total Aβ and Aβ1-40 was not significantly different from the control group. In other words, soluble Aβ is reduced less than plaque Aβ. However, detailed time course studies must be performed to determine further any changes in the equilibrium between soluble- and plaque Aβ. These findings indirectly demonstrate the importance of Aβ1-42 for plaque maintenance. Overall, it is likely that several different mechanisms may result in reduction of cerebral amyloid burden, depending on the animal model and the properties of the peptide used for immunization.

Numerous studies have suggested that amyloid deposition can activate inflammatory cascades in the brain, such as increased IL-1 production associated with neuronal injury and death (Sigurdsson et al., 1996 and Akiyama et al., 2000). It is possible that our immunization with Aβ homologous peptides could also stimulate such negative inflammatory pathways, along with amyloid reduction. However, few phagocytic microglia were observed in our immunized animals, as identified by OX-42 immunoreactivity or tomato lectin binding. This is not surprising because after 7 months treatment most of the plaques have been cleared. Furthermore, in the immunized group of mice microglial IL-1β staining was virtually absent, whereas numerous ramified IL-1β positive microglia were associated with the plaques in the control Tg group. The laboratory of the present inventors have previously reported a similar lack of IL-1β staining in a rat model of cerebral amyloidosis following treatment with a β-sheet breaker peptide (Sigurdssone et al., 2000). However, in that acute study (16 days) this effect was associated with extensive increase in phagocytic OX-42 staining, indicating that phagocytes do not express IL-1β. The current observations from the experiments in this example may suggest that an important effect of the immunization is reduced inflammation within the brain.

EXAMPLE 2

MATERIALS AND METHODS

Peptides

The peptides used (Aβ1-40, Aβ1-42, Aβ1-30-NH$_2$, K6Aβ1-30-NH$_2$, Aβ1-30-K6 (SEQ ID NO:11), Aβ1-30-NH$_2$(EE$_{18,19}$) (SEQ ID NO:12), Aβ1-30-NH$_2$(DD$_{18,19}$) (SEQ ID NO:13) were synthesized at the Keck Foundation (Yale University, New Haven, Conn.), as described previously (Sigurdsson et al., 2000). The Aβ homologous peptides maintain the two major immunogenic sites of Aβ peptides (residues 1–11 and 22–28 of Aβ1-42 based on the antigenic index of Jameson et al. (1998) and on preliminary results obtained in the laboratory of the present inventors), while being non-fibrillar and non-toxic.

Study of Amyloid Fibril Formation in Vitro and Neurotoxicity

The experiments were performed as described in Example 1.

Data Analysis

Data Analysis: The cell culture data was analyzed by one-way ANOVA, followed by a Newman Keuls'test for post hoc analysis (GraphPad Prism 3.0).

RESULTS

Figure 5:
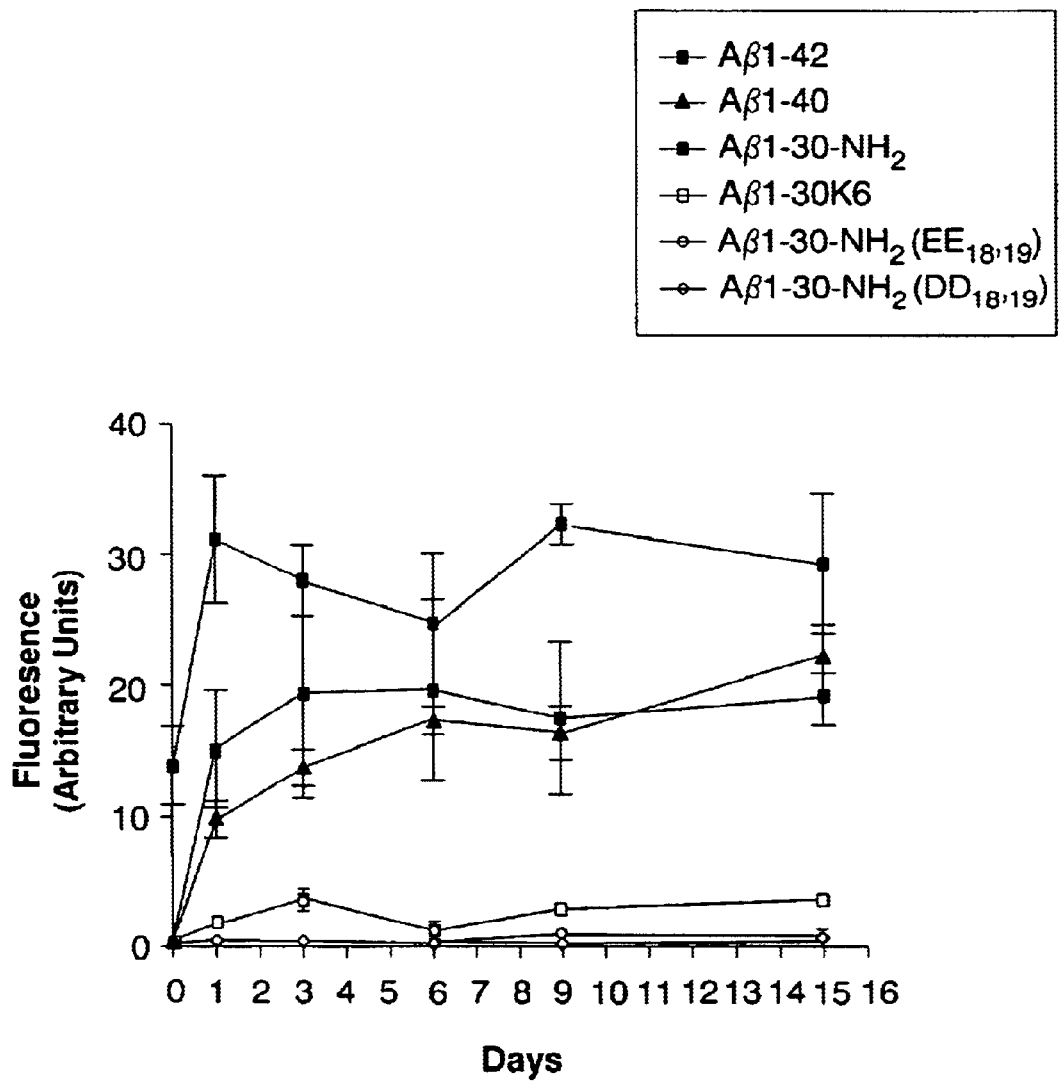
FIG. 5 shows the results of a thioflavin T fluorometric assay. Fibril formation of Aβ1-42, Aβ1-40, Aβ1-30-NH$_2$, Aβ1-30K6, Aβ1-30-NH$_2$(EE$_{18,19}$) and Aβ1-30-NH$_2$(DD$_{18,19}$) was measured in vitro following incubation at 37° C.

Thioflavin T assay: Aβ1-42 was already fibrillar at t=0, whereas Aβ1-30-NH$_2$ and Aβ1-40 gradually formed fibrils over time (FIG. 5). Aβ1-30K6 was slightly fibrillogenic but Aβ1-30-NH$_2$(EE$_{18,19}$) and Aβ1-30-NH$_2$(DD$_{18,19}$) did not form fibrils following incubation at 37° C. for at least 15 days.

Figure 6A:
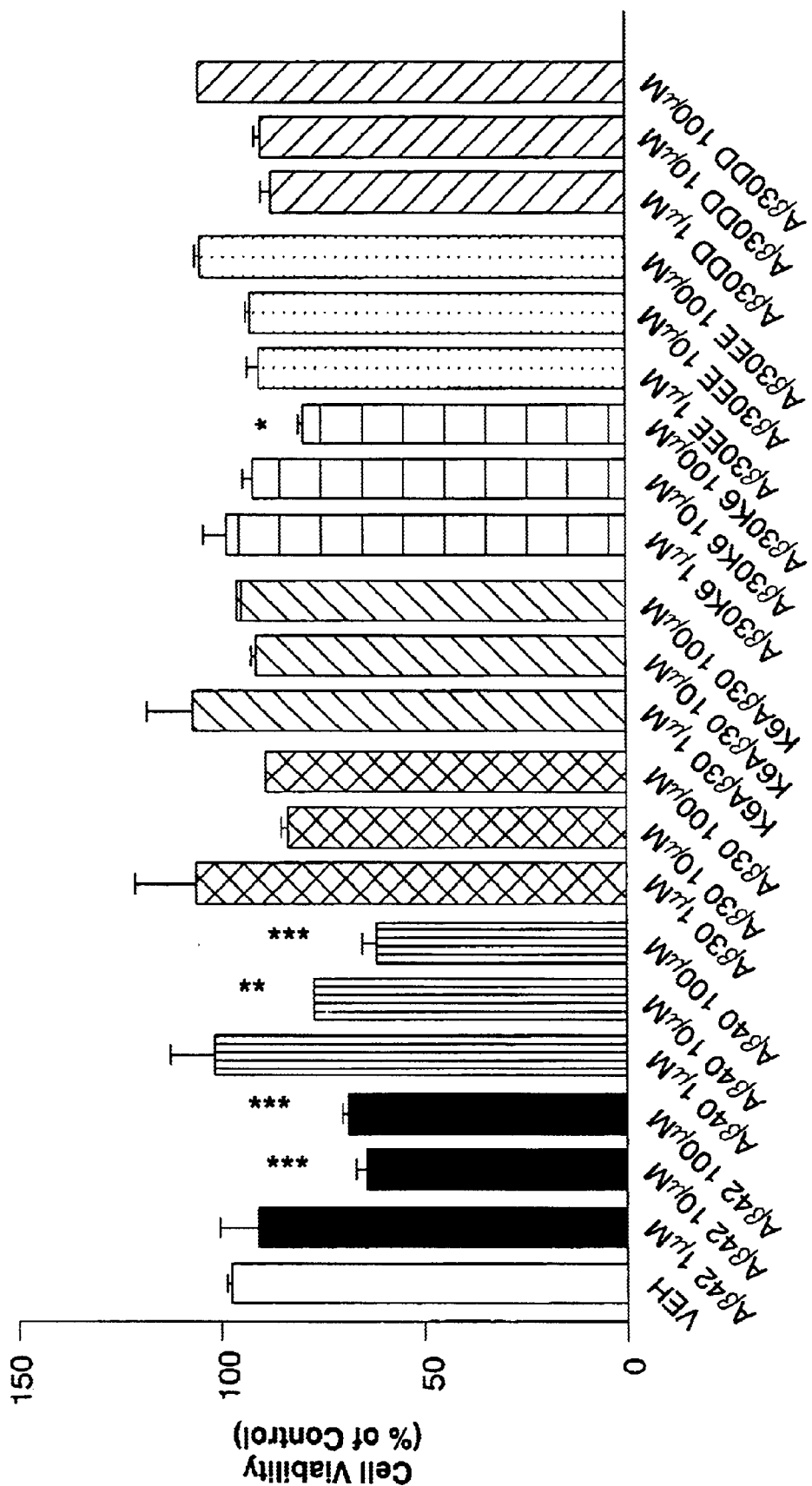
FIGS. 6A and 6B show the results of MTT cell toxicity assay. Neurotoxicity of Aβ1-42, Aβ1-40, Aβ1-30-NH$_2$1 K6Aβ1-30-NH$_2$, Aβ1-30K6, Aβ1-30-NH$_2$(EE$_{18,19}$) and Aβ1-30-NH$_2$(DD$_{18,19}$) was determined following treatment of human neuroblastoma cells (SK-N-SH) for 2 (FIG. 6A) and 6 (FIG. 6B) days. *p<0.05; p<0.01; *p<0.001 compared to VEH group (one-way ANOVA)
Figure 6B:
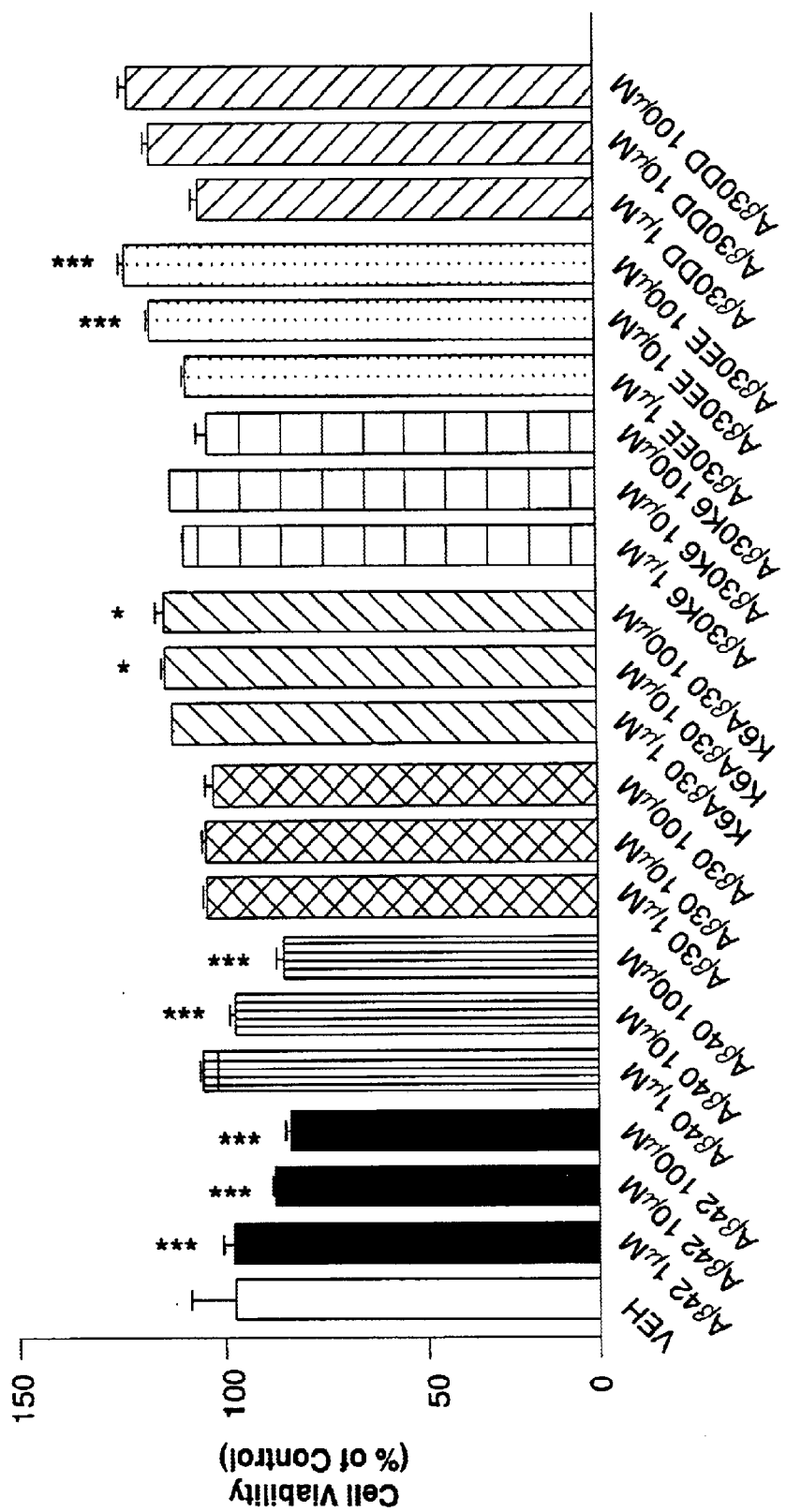

Neurotoxicity: To further assess the safety of this vaccination approach the neurotoxicity of the peptides was determined (FIGS. 6A and 6B). Treatment effect was observed both at 2 and 6 days (p<0.0001). The control peptides Aβ1-40 and Aβ1-42 were toxic (p<0.01–0.001) to the human neuroblastoma cells (SK-N-SH), compared to vehicle group, as determined by the MTT assay. K6Aβ-30-NH$_2$ had no effect on cell viability at 2 days and was slightly trophic at 6 days (p<0.001), and the highest dose (100 μM) of Aβ1-30K6 was slightly toxic following 2 days treatment but not at 6 days. During the incubation period, aggregates were visible under the microscope only in culture wells containing Aβ1-42 (10–100 μM). These Aβ homologous peptides according to the present invention do not form fibrils and are non-toxic in human neuronal culture. Overall, this approach has a much lower risk of leading to toxic effects in humans, than the use of Aβ1-40/42.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aguado et al., *Vaccine* 17:2321–2328 (1999)
Aucouturier et al., Biochemical and conformational variability of human prion strains in sporadic Creutzfeldt-Jakob disease, *Neurosci. Lett.* 274:33–36 (1999)
Barrow et al., *J. Mol. Biol.* 225:1075–1093 (1992)
Barrow et al., *J. Mol. Biol.* 225:1075–1093 (1992)
Better et al., *Science* 240:1041–1043, (1988)
Boulianne et al., "Production of functional chimaeric mouse/human antibody", *Nature* 312:643–646, (1984)
Brett et al., *Eur. J. Immunol.* 23:1608 (1993)
Burdick et al., *J. Biol. Chem.* 267:546–564 (1992)
Burdick et al., *J. Biol. Chem.* 267:546–554 (1992)
Bushchle et al., "Transloading of tumor antigen-derived peptides into antigen-presenting cells", *Proc Natl Acad Sci USA*, 94:(7)3256–61 (1997)
Bush et al., *Science* 265:1464–1467 (1994)
Cabilly et al., *Proc. Natl. Acad. Sci. USA* 81:3273–3277, (1984)
Cabilly et al., European Patent Application 125.023 (published Nov. 14, 1984)
Castaño et al., Fibrillogenesis in Alzheimer's disease of amyloid beta peptides and apolipoprotein E, *Biochem. J.* 306:599–604 (1995)
Castaño et al., In vitro formation of amyloid fibrils from two synthetic peptides of different lengths homologous to Alzheimer's disease beta-protein, *Biochem. Biophys. Res. Commun* 141:782–789 (1986)
Colligan et al., *Current Protocols in Immunology*, Green Publishing Assoc., and Wiley Interscience, New York, (1993)
Deierkauf et al., "Phygocytosis by rabbit polymorphonuclear leukocytes: the effect of albumin and polyamine acids on latex uptake", *J Cell Physiol*, 92(2):169–75 (1977)
DiNicola et al., "Large-scale feasibility of gene transduction into human cd34+ cell-derived dendritic cells by adenoviral/polycation complex", *Br J Haematol*, 111(1):344–50 (2000)
Eshhar et al., *Br. J. Cancer Suppl.*, 10:27–9 (1990)
Exley et al., *FEBS Lett.* 324:293–295 (1993)
Forsell et al., *Neurosci. Lett.* 184:90–93 (1995)
Games et al., *Nature* 373:523–527 (1995)
Ghiso et al. *Biochem. J.* 293:27–30 (1994)
Ghiso et al., Epitope map of two polyclonal antibodies that recognize amyloid lesions in patients with Alzheimer's disease, *Biochem. J.* 282:517–522 (1992)
Golabek et al., "The interaction between apolipoprotein E and Alzheimer's amyloid p-peptide is dependent on p-peptide conformation", *J. Biol. Chem.* 271:10602–10606 (1996)
Gross et al., *Proc. Natl. Acad. Sci. USA*, 86:10024–8 (1989)
Harlow et al., *ANTIBODIES: A LABORATORY MANUAL*, Cold Spring Harbor Laboratory, Cold Spring Harbor, N.Y. (1988)
Hilbich et al., *J. Mol. Biol.* 228:460–473 (1992)
Holcomb et al., Accelerated Alzheimer-type phenotype in transgenic mice carrying both mutant amyloid precursor protein and presenilin 1 transgenes, *Nat. Genet.* 4:97–100 (1998).
Hsiao et al., Correlative memory deficits, Aβ elevation and amyloid plaques in transgenic mice, *Science* 274:99–102 (1996)
Isberg et al., *Cell* 60:861 (1990)
Jameson et al., The Antigenic Index: A Novel Algorithm for Predicating Antigenic Determinants, *Comput. Appl. Biosci.* 4:181–186 (1988)
Jarrett et al., *Biochem.* 32 :4693–4697 (1993)
Jarrett et al., *Cell* 73:1055–1058 (1993)
Jarrett et al., *Biochem* 32:4693–4697 (1993)
Kang et al. *Nature* 325:503–507, 1987; Dyrks et al. *EMBO J.* 7:949–957, (1988)
Kisilevsky et al., *Nature Medicine* 1(2):143–148 (1995)
Kohler et al., *Nature* 256:495–497 (1975)
Koudinov et al., *Biochem. Biophys. Res. Commun.* 205:1164–1171, (1994)
Kudo et al., European Patent Application 184187 (published Jun. 11, 1986)
LeVine, Thioflavine T interaction with synthetic Alzheimer's disease β-amyloid proteins: detection of amyloid aggregation in solution, *Protein Sci.* 2:404–410 (1993)
Liu et al., *Proc. Natl. Acad. Sci USA* 84:3439–3443, (1987)
Martinez-Fong et al., "Nonenzymatic glycosylation of poly-L-lysine: a new tool for targeted gene delivery", *Hepatology*, 20(6):1602–8 (1994)
Merlini et al., *Proc. Natl. Acad. Sci. USA* 92:2959–2963 (1995)
Morrison et al., European Patent Application 173494 (published Mar. 5, 1986)
Morrison et al., *Proc. Natl. Acad. Sci. USA* 81:6851–6855, (1984)
Muller-Hill and Beyreuther, *Ann. Rev. Biochem.* 38:287–307 (1989)
Neuberger et al., PCT Application WO 8601533, (published Mar. 13, 1986)
Neuberger et al., *Nature* 314:268–270, (1985)
O'Hagan et al., *Vaccine* 9:768–771 (1991)
O'Hagan et al., *Molec. Immunol.* 28:287–294 (1991)
Pallitto et al., *Biochemistry* 38:3570–3578 (1999)
Peterson et al., "Polyamino acid enhancement of bacterial phagocytosis by human polymorphonuclear leukocytes and peritoneal macrophages", *Infect Immun* 43(2):561–6 (1984)
Robinson et al., International Patent Publication WO 9702671 (published May 7, 1987)
Sahagan et al., *J. Immunol.* 137:1066–1074, (1986)
Schenk et al., Immunization with Amyloid-β Attenuates Alzheimer Disease-like Pathology in the PDAPP Mouse, *Nature* 400:173–177 (1999)
Seubert et al., *Nature* 359:355–327 (1992)
Shen et al., "Disulfide spacer between methotrexate and poly(D-lysine). A probe for exploring the reductive process in endocytosis", *J. Biol. Chem*, 260(20):10905–8 (1985)
Shoji et al., Science 258:126–129 (1992)
Sigurdsson et al., In Vivo reversal of amyloid-β lesions in rat brain, *J. Neuropath. Exp. Neurol.* 59:11–17 (2000)
Sigurdsson et al., Local and distant histopathological effects of unilateral amyloid-beta 25–35 injections into the amygdala of young F344 rats, *Neurobiol. Aging* 17:893–901 (1996)

Soto et al., "β-sheet breaker peptides inhibit fibrillogenesis in a rat brain model of amyloidosis: potential Alzheimer's therapy" *Nat. Med.* 4:822–826 (1998)

Soto et al., Alzheimer's soluble p-amyloid is conformationally modified by apolipoproteins in vitro, *Neuroreport* 7:721725 (1996)

Soto et al., *Biochem. J.* 314:701–707 (1996)

Soto et al., The alpha-helical to beta-strand transition in the amino-terminal fragment of the amyloid beta-peptide modulates amyloid formation, *J. Biol. Chem.* 270:3063–3067 (1995)

Soto et al., Apolipoprotein E increases the fibrillogenic potential of synthetic peptides derived from Alzheimer's, gelsolin and AA amyloids, *FEBS Lett.* 371:110–114 (1995)

Soto et al. *J. Neurochem.* 63:1191–1198 (1994)

Strittmatter et al., *Proc. Natl. Acad. Sci. USA* 90:1977–1981, (1993)

Sun et al., *Proc. Natl. Acad. Sci. USA* 84:214–218, (1987)

Surewicz et al., Determination of protein secondary structure by Fourier transform infrared spectroscopy: a critical assessment, *Biochem.* 32:389–394 (1993)

Taniguchi et al., European Patent Application 171496 (published Feb. 19, 1985)

Tran Van Nhieu et al., *J. Biol. Chem.* 266:24367 (1991)

Wang et al., "Endocytosis of horseradish peroxidase-polylysine conjugate by glomerular epithelial cells: an in vivo study", *J. Pathol.*, 159(2):159–67 (1989)

Wisniewski et al., Acceleration of Alzheimer's fibril formation by apolipoprotein E in vitro, *Am. J. Pathol.* 145:1030–1035 (1994)

Wisniewski et al., Cerebrospinal fluid inhibits Alzheimer beta-amyloid fibril formation in vitro, *Ann. Neurol.* 34:631–633 (1993)

Wisniewski et al., Peptides homologous to the amyloid protein of Alzheimer's disease containing a glutamine for glutamic acid substitution have accelerated amyloid fibril formation, *Biochem. Biophys. Res. Commun.* 179:1247–1254 (1991)

Wisniewski et al., *Ann. Neurol.* 17:278–282 (1985)

Wood et al., *Biochemistry* 34:724–730 (1995)

Zagorski et al., *Biochem.* 31:5621–5631 (1992)

Zlokovic et al., *Proc. Natl. Acad. Sci. USA* 93:4229–04233 (1996)

Zlokovic et al., *Biochem. Biophys. Res. Commun.* 205:1431–1437 (1994)

---

SEQUENCE LISTING

<160> NUMBER OF SEQ ID NOS: 15

<210> SEQ ID NO 1
<211> LENGTH: 30
<212> TYPE: PRT
<213> ORGANISM: Artificial
<220> FEATURE:
<223> OTHER INFORMATION: Synthetic

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala
            20                  25                  30

<210> SEQ ID NO 2
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 7-10 either are present,
      together as all Lys or all Asp or are all absent. When residues
      7-10 are present the n any one or all of residues 1-6 can either
      be absent or present as Lys or Asp to form, in combination with
      residues 7-10, a
<220> FEATURE:
<223> OTHER INFORMATION: N-terminal polylysine or polyaspartate segment
      of 4-10 residues in length
<220> FEATURE:
<221> NAME/KEY: misc_feature
<223> OTHER INFORMATION: Amino acid residues 27-31 are LeuValPhePheAla
      in which one or two of residues 27-31 are substituted with Lys,
      Asp, or Glu. The C- terminal Ala residue may be amidated

<400> SEQUENCE: 2

Xaa Xaa Xaa Xaa Xaa Xaa Xaa Xaa Xaa Xaa Asp Ala Glu Phe Arg His
1               5                   10                  15

```
Asp Ser Gly Tyr Glu Val His His Gln Lys Xaa Xaa Xaa Xaa Xaa Glu
            20                  25                  30

Asp Val Gly Ser Asn Lys Gly Ala
            35                  40

<210> SEQ ID NO 3
<211> LENGTH: 70
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 7-10 either are all Lys
      or all Asp or are all absent.  When residues 7-10 are present,
      then any one or all of amino acid residues 1-6 can
      either be absent or present as Lys or Asp to form,
      in combination with residues 7-10, a N-terminal
<220> FEATURE:
<223> OTHER INFORMATION: polylysine or polyaspartate segment of 4 to 10
      residues in length
<220> FEATURE:
<221> NAME/KEY: misc_feature
<223> OTHER INFORMATION: Amino acid residues 27-31 and 57-61 are the
      same and are LeuValPhePheAla in which one or two of residues 27-31
      and the same one or two residues of residues 57-61
      are substituted with Lys, Asp, or Glu.
      The C-terminal Ala residue may be amidated

<400> SEQUENCE: 3

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Asp Ala Glu Phe Arg His Asp Ser
            35                  40                  45

Gly Tyr Glu Val His His Gln Lys Xaa Xaa Xaa Xaa Xaa Glu Asp Val
        50                  55                  60

Gly Ser Asn Lys Gly Ala
65                  70

<210> SEQ ID NO 4
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 31-34 either are all Lys or
      all Asp or are all absent.  When all residues
      31-34 are present, then any one or all of residues
      35-40 can either be absent or present as Lys or Asp to form,
      in combination with residues 31-34, a C-terminal
<220> FEATURE:
<223> OTHER INFORMATION: polylysine or polyaspartate segment of 4-10 residues in length
<220> FEATURE:
<221> NAME/KEY: misc_feature
<223> OTHER INFORMATION: Amino acid residues 17-21 are LeuValPhePheAla
      in which one or two of residues 17-21 are substituted with Lys,
      Asp, or Glu

<400> SEQUENCE: 4

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Xaa Xaa
            20                  25                  30

Xaa Xaa Xaa Xaa Xaa Xaa Xaa Xaa
```

35            40

<210> SEQ ID NO 5
<211> LENGTH: 70
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 61-64 either are all Lys
      or all Asp, or are all absent.  When all residues 61-64
      are present, then any one or all of residues 65-70
      can either be Lys or Asp to form, in combination
      with residues 61-64, a C-terminal polylysine or
<220> FEATURE:
<223> OTHER INFORMATION: polyaspartate segment of 4 to 10 residues in
      length
<220> FEATURE:
<221> NAME/KEY: misc_feature
<223> OTHER INFORMATION: Amino acid residues 17-21 and 47-51 are
      LeuValPhePheAla in which one or two
      of residues 17-21 and 47-51 are the same
      one or two residues substituted with Lys, Asp, or Glu

<400> SEQUENCE: 5

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala Asp Ala
            20                  25                  30

Glu Phe Arg His Asp Ser Gly Tyr Glu Val His His Gln Lys Xaa Xaa
        35                  40                  45

Xaa Xaa Xaa Glu Asp Val Gly Ser Asn Lys Gly Ala Xaa Xaa Xaa Xaa
    50                  55                  60

Xaa Xaa Xaa Xaa Xaa Xaa
65                  70

<210> SEQ ID NO 6
<211> LENGTH: 36
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: C-terminal residue 36 may be amidated.

<400> SEQUENCE: 6

Lys Lys Lys Lys Lys Lys Asp Ala Glu Phe Arg His Asp Ser Gly Tyr
1               5                   10                  15

Glu Val His His Gln Lys Leu Val Phe Phe Ala Glu Asp Val Gly Ser
            20                  25                  30

Asn Lys Gly Ala
        35

<210> SEQ ID NO 7
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 1-6 can either be absent or
      present as Lys or Asp to form,
      in combination with residues 7-10, a N-terminal
      polylysine or polyaspartate segment of 4-10 residues in length
<220> FEATURE:

```
<221> NAME/KEY: misc_feature
<223> OTHER INFORMATION: The C-terminal Ala residue may be amidated.

<400> SEQUENCE: 7

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Leu Val Phe Phe Ala Glu
            20                  25                  30

Asp Val Gly Ser Asn Lys Gly Ala
        35                  40

<210> SEQ ID NO 8
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 35-40 can either be absent
      or present as Lys or Asp to form, in combination
      with residues 31-34, a C-terminal polylysine or
      polyaspartate segment of 4-10 residues in length

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Xaa Xaa
            20                  25                  30

Xaa Xaa Xaa Xaa Xaa Xaa Xaa Xaa
        35                  40

<210> SEQ ID NO 9
<211> LENGTH: 50
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 7-10 either are present,
      together as all Lys or all Asp or are all absent.
      When residues 7-10 are present the n any one or all
      of residues 1-6 can either be absent or present
      as Lys or Asp to form, in combination with residues 7-10, a
<220> FEATURE:
<223> OTHER INFORMATION: N-terminal polylysine or polyaspartate segment
      of 4-10 residues in length
<220> FEATURE:
<221> NAME/KEY: misc_feature
<223> OTHER INFORMATION: Amino acid residues 27-31 are LeuValPhePheAla
      in which one or two of residues 27-31 are substituted with Lys,
      Asp, or Glu.
<220> FEATURE:
<221> NAME/KEY: misc_feature
<223> OTHER INFORMATION: Amino acid residues 45-50 can either be absent
      or present as Lys or Asp to form, in combination with residues
      41-44, a C-terminal polysine or polyaspartate
      segment of 4-10 residues

<400> SEQUENCE: 9

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Xaa Xaa Xaa Xaa Xaa Xaa Xaa Xaa
        35                  40                  45
```

```
Xaa Xaa
    50

<210> SEQ ID NO 10
<211> LENGTH: 80
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 7-10 either are all Lys or
      all Asp or are all absent.  When residues 7-10 are
      present, then any one or all of amino acid residues
      1-6 can either be absent or present as Lys or
      Asp to form, in combination with residues 7-10, a N-terminal
<220> FEATURE:
<223> OTHER INFORMATION: polylysine or polyaspartate segment of 4 to 10
      residues in length
<220> FEATURE:
<221> NAME/KEY: misc_feature
<223> OTHER INFORMATION: Amino acid residues 75-80 can either be absent
      or present as Lys or Asp to form, in combination with residues
      71-74, a C-terminal polylysine or polyaspartate
      segment of 4-10 residues
<220> FEATURE:
<221> NAME/KEY: misc_feature
<223> OTHER INFORMATION: Amino acid residues 27-31 and 57-61 are the
      same and are LeuValPhePheAla in which one or two of residues 27-31
      and the same one or two residues of residues 57-61 are substituted
      with Lys, Asp, or Glu.

<400> SEQUENCE: 10

Xaa Xaa Xaa Xaa Xaa Xaa Xaa Xaa Xaa Xaa Asp Ala Glu Phe Arg His
1               5                   10                  15

Asp Ser Gly Tyr Glu Val His His Gln Lys Xaa Xaa Xaa Xaa Xaa Glu
            20                  25                  30

Asp Val Gly Ser Asn Lys Gly Ala Asp Ala Glu Phe Arg His Asp Ser
        35                  40                  45

Gly Tyr Glu Val His His Gln Lys Xaa Xaa Xaa Xaa Xaa Glu Asp Val
    50                  55                  60

Gly Ser Asn Lys Gly Ala Xaa Xaa Xaa Xaa Xaa Xaa Xaa Xaa Xaa Xaa
65                  70                  75                  80

<210> SEQ ID NO 11
<211> LENGTH: 36
<212> TYPE: PRT
<213> ORGANISM: Artificial
<220> FEATURE:
<223> OTHER INFORMATION: Synthetic

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Lys Lys
            20                  25                  30

Lys Lys Lys Lys
        35

<210> SEQ ID NO 12
<211> LENGTH: 30
<212> TYPE: PRT
<213> ORGANISM: Artificial
<220> FEATURE:
<223> OTHER INFORMATION: Synthetic

<400> SEQUENCE: 12
```

```
Asp Ala Glu Phe Arg His Asp Ser Gly Tyr Glu Val His His Gln Lys
1               5                   10                  15

Leu Glu Glu Phe Ala Glu Asp Val Gly Ser Asn Lys Gly Ala
            20                  25                  30

<210> SEQ ID NO 13
<211> LENGTH: 30
<212> TYPE: PRT
<213> ORGANISM: Artificial
<220> FEATURE:
<223> OTHER INFORMATION: Synthetic

<400> SEQUENCE: 13

Asp Ala Glu Phe Arg His Asp Ser Gly Tyr Glu Val His His Gln Lys
1               5                   10                  15

Leu Asp Asp Phe Ala Glu Asp Val Gly Ser Asn Lys Gly Ala
            20                  25                  30

<210> SEQ ID NO 14
<211> LENGTH: 5
<212> TYPE: PRT
<213> ORGANISM: Artificial
<220> FEATURE:
<223> OTHER INFORMATION: Synthetic

<400> SEQUENCE: 14

Leu Pro Phe Phe Asp
1               5

<210> SEQ ID NO 15
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Amino acid residues 17-21 are LeuValPhePheAla
      in which one or two of residues 17-21 are substituted with Lys,
      Asp, or Glu.

<400> SEQUENCE: 15

Asp Ala Glu Phe Arg His Asp Ser Gly Tyr Glu Val His His Gln Lys
1               5                   10                  15

Xaa Xaa Xaa Xaa Xaa Glu Asp Val Gly Ser Asn Lys Gly Ala
            20                  25                  30
```

What is claimed is:

1. An isolated peptide comprising the amino acid sequence
    (Asp Ala Glu Phe Arg His Asp Ser Gly Tyr Glu Val His His Gln Lys Xaa$_1$ Xaa$_2$ Xaa$_3$ Xaa$_4$ Xaa$_5$ Glu Asp Val Gly Ser Asn Lys Gly Ala)$_n$ (SEQ ID NO:15)
    wherein n is 1 or 2; and
    Xaa$_1$, Xaa$_2$, Xaa$_3$, Xaa$_4$, and Xaa$_5$ are Leu, Val, Phe, Phe, and Ala, respectively, in which one or two of residues Xaa$_1$, Xaa$_2$, Xaa$_3$, Xaa$_4$, and Xaa$_5$ is substituted with Lys, Asp, or Glu.
2. The peptide of claim 1, further comprising at least one N- or C-terminal sequence of 4 to 10 Lys or Asp residues.
3. The peptide of claim 2, wherein the N-terminal sequence comprises 4–10 Lys or Asp residues.
4. The peptide of claim 3, wherein the C-terminus of said peptide is amidated.
5. The peptide of claim 3, wherein the N-terminal sequence comprises 4 to 10 Lys residues.
6. The peptide of claim 3, wherein the N-terminal sequence comprises 4 to 10 Asp residues.
7. The peptide of claim 3, wherein the amino acid sequence of said peptide is SEQ ID NO:2.
8. The peptide of claim 3, wherein the amino acid sequence of said peptide is SEQ ID NO:3.
9. The peptide of claim 2, comprising a C-terminal sequence of 4–10 Lys or Asp residues.
10. The peptide of claim 9, wherein the C-terminal sequence comprises 4 to 10 Lys residues.
11. The peptide of claim 9, wherein the C-terminal sequence comprises 4 to 10 Asp residues.
12. The peptide of claim 9, wherein the amino acid sequence of said peptide is SEQ ID NO:4.
13. The peptide of claim 9, wherein the amino acid sequence of said peptide is SEQ ID NO:5.
14. A conjugate comprising the peptide of claim 2 cross-linked to a polymer molecule.

15. The conjugate according to claim 14, wherein said polymer molecule is a polypeptide comprising a promiscuous T helper cell epitope.

16. The conjugate according to claim 15, wherein said promiscuous T helper cell epitope is a promiscuous T helper cell epitope of tetanus toxin, pertussis toxin, diphtheria toxin, measles virus, hepatitis B virus surface antigen, *Chlamydia tracomatis* major outer membrane protein, *Plasmodium falciparum* circumsporozoite, *Schistosoma mansoni* triose phosphate isomerase, or *Escherichia coli* TraT.

17. The conjugate according to claim 14, wherein said polymer is selected from the group consisting of mannan, glucan, tripalmitoyl-5-glycerine cysteine, and poly(lactide-co-glycolide).

18. An immunizing composition, comprising an immunizing effective amount of the isolated peptide according to claim 2 or a conjugate thereof and a pharmaceutically acceptable carrier, excipient, diluent, or auxiliary agent.

19. The immunizing composition according to claim 18, wherein said pharmaceutically acceptable auxiliary agent is an adjuvant.

20. The immunizing composition according to claim 19, wherein said adjuvant is alum.

21. The peptide of claim 1, comprising an N-terminal sequence of 4 to 10 Lys or Asp residues and a C-terminal sequence of 4 to 10 Lys or Asp residues.

22. The peptide of claim 1, wherein the amino acid sequence of said peptide is selected from the group consisting of SEQ ID NO:9 and SEQ ID NO:10.

23. The peptide of claim 1, wherein the amino acid sequence of said peptide is selected from the group consisting of SEQ ID NO:12, and SEQ ID NO:13.

24. A conjugate comprising the peptide of claim 1 cross-linked to a polymer molecule.

25. The conjugate according to claim 24, wherein said polymer molecule is a polypeptide comprising a promiscuous T helper cell epitope.

26. The conjugate according to claim 25, wherein said promiscouos T helper cell epitope is a promiscuous T helper cell epitope of tetanus toxin, pertussis toxin, diphtheria toxin, measles virus, hepatitis B virus surface antigen, *Chlamydia tracomatis* major outer membrane protein, *Plasmodium falciparu m* circumsporozoite, *Schistosoma mansoni* triose phosphate isomerase, or *Escherichia coli* TraT.

27. The conjugate according to claim 24, wherein said polymer is selected from the group consisting of mannan, glucan, tripalmitoyl-5-glycerine cysteine, and poly(lactide-co-glycolide).

28. An immunizing composition, comprising an immunizing effective amount of the isolated peptide according to claim 1 or a conjugate thereof and a pharmaceutically acceptable carrier, excipient, diluent, or auxiliary agent.

29. The immunizing composition according to claim 28, wherein said pharmaceutically acceptable auxiliary agent is an adjuvant.

30. The immunizing composition according to claim 29, wherein said adjuvant is alum.

* * * * *